(12) United States Patent
Van Voorst et al.

(10) Patent No.: US 9,811,001 B2
(45) Date of Patent: Nov. 7, 2017

(54) METHOD AND APPARATUS FOR INSPECTION AND METROLOGY

(71) Applicant: ASML NETHERLANDS B.V., Veldhoven (NL)

(72) Inventors: Peter Danny Van Voorst, Nijmegen (NL); Duygu Akbulut, Eindhoven (NL); Koos Van Berkel, Waalre (NL); Jeroen Johan Maarten Van De Wijdeven, Eindhoven (NL); Ferry Zijp, Nuenen (NL)

(73) Assignee: ASML NETHERLANDS B.V., Veldhoven (NL)

( * ) Notice: Subject to any disclaimer, the term of this patent is extended or adjusted under 35 U.S.C. 154(b) by 31 days.

(21) Appl. No.: 15/065,674

(22) Filed: Mar. 9, 2016

(65) Prior Publication Data
US 2016/0266503 A1 Sep. 15, 2016

(30) Foreign Application Priority Data
Mar. 11, 2015 (EP) ..................................... 15158677

(51) Int. Cl.
*G01B 11/04* (2006.01)
*G02B 7/02* (2006.01)
(Continued)

(52) U.S. Cl.
CPC .......... *G03F 7/70483* (2013.01); *G01B 11/00* (2013.01); *G01N 21/956* (2013.01);
(Continued)

(58) Field of Classification Search
CPC .......... G01B 9/04; G01B 11/00; G01B 11/02; G01B 2210/56; G01N 21/0016;
(Continued)

(56) References Cited

U.S. PATENT DOCUMENTS 6,738,323 B1 5/2004 Imanishi et al.
7,791,732 B2 9/2010 Den Boef et al.
(Continued)

FOREIGN PATENT DOCUMENTS

EP 0864899 9/1998
JP 2006-215004 8/2006
(Continued)

OTHER PUBLICATIONS

Ferry Zijp, "Near-Field Optical Data Storage," Technische Universiteit Delft, ISBN 978-90-9022391-9 / NUR 926, 251 pages (2007).
(Continued)

*Primary Examiner* — Colin Kreutzer
(74) *Attorney, Agent, or Firm* — Pillsbury Winthrop Shaw Pittman LLP

(57) ABSTRACT

A method of position control of an optical component relative to a surface is disclosed. The method may include: obtaining a first signal by a first position measurement process; controlling relative movement between the optical component and the surface for a first range of motion using the first signal; obtaining a second signal by a second position measurement process different than the first position measurement process; and controlling relative movement between the optical component and the surface for a second range of motion using the second signal, the second range of motion being nearer the surface than the first range of motion.

20 Claims, 12 Drawing Sheets

(51) Int. Cl.
  *G03B 27/32* (2006.01)
  *G03B 27/74* (2006.01)
  *G03F 7/20* (2006.01)
  *G02B 21/00* (2006.01)
  *G01N 21/956* (2006.01)
  *G01B 11/00* (2006.01)
  *G02B 27/09* (2006.01)

(52) U.S. Cl.
  CPC ..... *G02B 21/0016* (2013.01); *G02B 27/0988* (2013.01); *G03F 7/70625* (2013.01); *G03F 7/70633* (2013.01)

(58) Field of Classification Search
  CPC .............. G01N 21/956; G02B 21/0016; G02B 27/0988; G03F 7/70483; G03F 7/70625; G03F 7/70633; G03F 7/70641; G03F 7/70825; G03F 9/703; G11B 7/1387
  USPC ........... 355/67, 68, 77; 356/237.5, 625, 635, 356/636; 359/823
  See application file for complete search history.

(56) References Cited

U.S. PATENT DOCUMENTS

| | | | |
|---|---|---|---|
| 7,889,624 B2 | 2/2011 | Watanabe | |
| 8,411,287 B2 | 4/2013 | Smilde et al. | |
| 9,081,303 B2 | 7/2015 | Cramer et al. | |
| 2006/0066855 A1 | 3/2006 | Den Boef et al. | |
| 2008/0198728 A1 | 8/2008 | Watanabe | |
| 2009/0316979 A1* | 12/2009 | Gidon ................ | G01B 11/24 382/145 |
| 2011/0027704 A1 | 2/2011 | Cramer et al. | |
| 2011/0043791 A1 | 2/2011 | Smilde et al. | |
| 2012/0044470 A1 | 2/2012 | Smilde et al. | |

FOREIGN PATENT DOCUMENTS

| | | | |
|---|---|---|---|
| JP | 2008-65931 | | 3/2008 |
| JP | 2009093745 A | * | 4/2009 |
| JP | 4626121 | | 2/2011 |
| WO | 2010/029471 | | 3/2010 |

OTHER PUBLICATIONS

International Search Report and Written Opinion dated Mar. 8, 2017 in corresponding International Patent Application No. PCT/EP2016/054310.

* cited by examiner

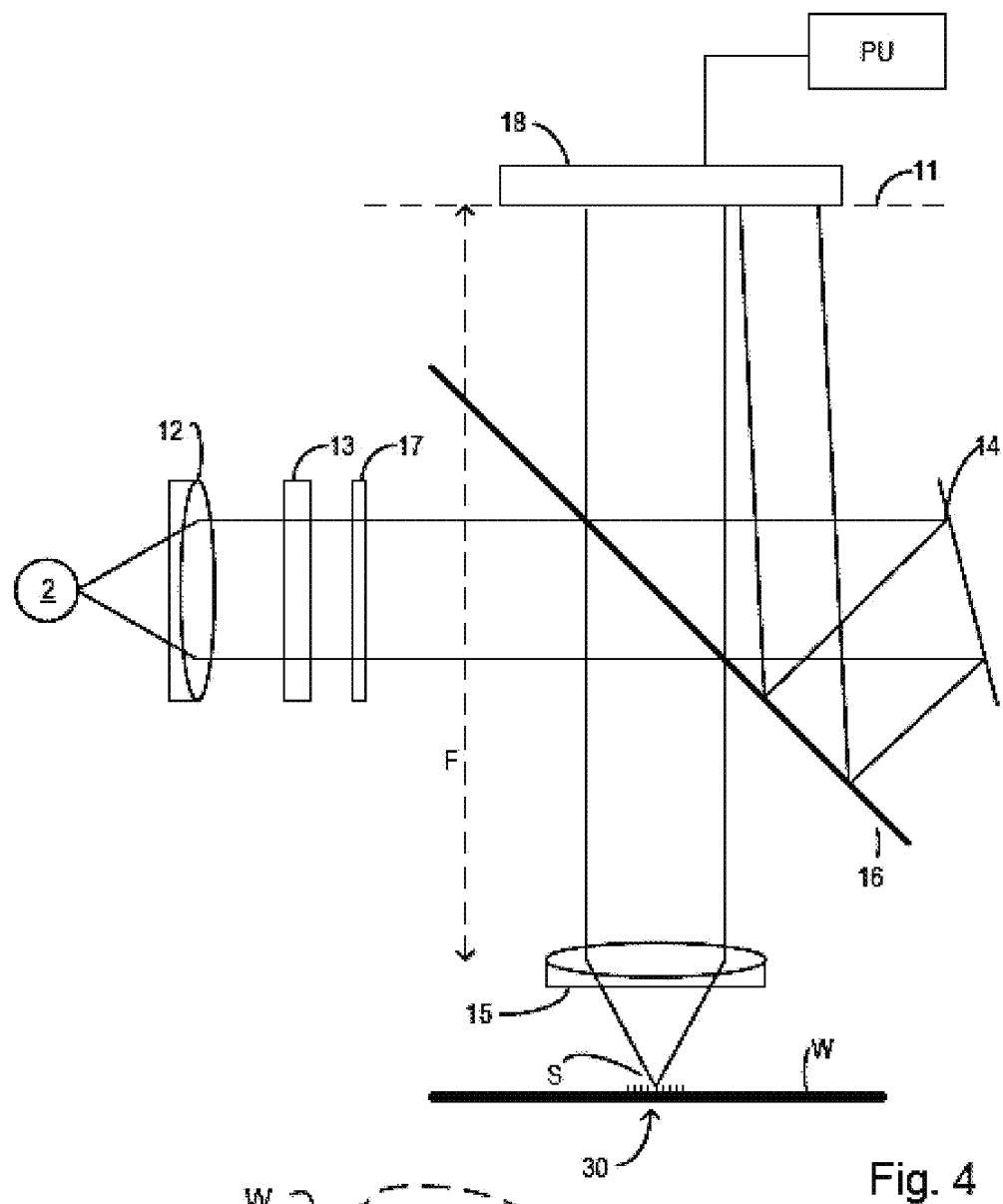
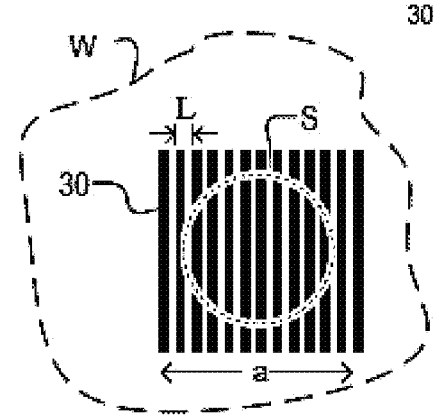
Fig. 4
Fig. 5

METHOD AND APPARATUS FOR INSPECTION AND METROLOGY

This application claims priority to European Patent Application No. 15158677.3, filed on Mar. 11, 2015, which is incorporated herein in its entirety by reference.

FIELD

The present description relates to a method and apparatus to control a distance between two objects.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In order to monitor the lithographic process, the patterned substrate is inspected and one or more parameters of the patterned substrate are measured. The one or more parameters may include, for example, the overlay error between successive layers formed in or on the patterned substrate and/or critical linewidth of developed photosensitive resist. This measurement may be performed on a target of the product substrate itself and/or on a dedicated metrology target provided on the substrate. There are various techniques for making measurements of the microscopic structures formed in lithographic processes, including the use of a scanning electron microscope and/or various specialized tools.

A fast and non-invasive form of specialized inspection tool is a scatterometer in which a beam of radiation is directed onto a target on the surface of the substrate and properties of the scattered or reflected beam are measured. By comparing one or more properties of the beam before and after it has been reflected or scattered by the substrate, one or more properties of the substrate can be determined. Two main types of scatterometer are known. A spectroscopic scatterometer directs a broadband radiation beam onto the substrate and measures the spectrum (intensity as a function of wavelength) of the radiation scattered into a particular narrow angular range. An angularly resolved scatterometer uses a relatively narrowband radiation beam and measures the intensity of the scattered radiation as a function of angle.

A particular application of scatterometry is in the measurement of feature asymmetry within a periodic target. This can be used as a measure of overlay error, for example, but other applications are also known. In an angle resolved scatterometer, asymmetry can be measured by comparing opposite parts of the diffraction spectrum (for example, comparing the $-1$st and $+1^{st}$ orders in the diffraction spectrum of a periodic grating). This can be done simply in angle-resolved scatterometry, as is described for example in U.S. patent application publication US2006-066855.

SUMMARY

With reduction of the physical dimensions in lithographic processing, there is demand to, for example, increase measurement accuracy and/or reduce the space occupied by targets dedicated to metrology or inspection. Image based scatterometry measurements have been devised to allow the use of smaller targets, by taking separate images of the target using $-1^{st}$ and $+1^{st}$ order radiation in turn. Examples of this image based technique are described in published U.S. patent application publication nos. US2011-0027704, US2011-0043791 and US2012-0044470, which are incorporated herein in their entirety by reference Demand for further reduction in target size and for improved accuracy continues, however, and existing techniques suffer from various constraints that make it difficult to maintain accuracy and/or reduce the size of the targets. Another way to improve on inspection and measurement techniques is to use a solid immersion lens (SIL) as the optical element nearest the substrate surface. The extreme proximity of the SIL with the substrate surface (e.g., target surface) results in near-field radiation with a very high effective numerical aperture (NA) larger than 1. Using a coherent or incoherent radiation source with this SIL allows a very small target to be inspected.

To take advantage of the increasing numerical aperture, the gap between the SIL and the substrate needs to be set to a desired value. For example, the gap may be within the range of $\lambda/40$ to $\lambda/8$ (where $\lambda$ is the wavelength of the measurement radiation) e.g., within the range of 10-100 nm or 10-50 nm, to have the SIL in effective optical contact with the substrate. An example optical gap measuring method and apparatus can involve detecting cross components of polarization in the high numerical aperture element. The cross polarized signal is then recorded by a detector and can be used as an input parameter into a gap control process. This cross polarized signal may also be normalized by the cross polarized signal detected at a large gap of several wavelengths. In another example, the gap may be controlled by reference to reflected laser radiation intensity. With any detecting method, the gap between the SIL (or other component) and the substrate (or other surface) needs to be established to be, and maintained at, a desired gap distance or distance range.

With such small gap distances and various surface topographies possible (whether expected or unexpected due to process variations), it is desired to provide one or more methods and apparatus to control the position of a component relative to a surface at solid immersion gap distances. So, as a particular application, an embodiment may be applied to controlling a gap between an optical element and a reflective or diffractive surface for, e.g., inspection of a layer manufactured by a lithographic technique to measure overlay error or other one or more other parameters.

In an aspect, there is provided a method of position control of an optical component relative to a surface, the method comprising: obtaining a first signal by a first position measurement process; controlling relative movement between the optical component and the surface for a first range of motion using the first signal; obtaining a second signal by a second position measurement process different than the first position measurement process; and controlling relative movement between the optical component and the surface for a second range of motion using the second signal, the second range of motion being nearer the surface than the first range of motion.

In an aspect, there is provided a method of position control of an optical component relative to a surface, the method comprising: providing radiation through the optical component to reach the surface; blocking at least part of the radiation redirected by the surface to cause a change of shape or size of illuminated area in a pupil, or conjugate thereof, as a function of change in position between the optical component and the surface; and detecting the redirected radiation of the illuminated area to produce a trigger signal based on which the position of the optical component with respect to the surface is controlled.

In an aspect, there is provided a method comprising: providing radiation through an optical component to reach a surface; causing a change of shape or size of an area illuminated by radiation redirected by the surface as a function of change in position between the optical component and the surface; detecting, using a detector, at least part of the redirected radiation after having passed through an aperture of a mask to produce a detection signal, the aperture spaced apart from the intersection of an optical axis of the redirected radiation with the mask; and deriving a trigger signal as a function of the detection signal and a filtered version of the detection signal.

In an aspect, there is provided a method comprising: providing radiation through an optical component to reach a surface; causing a change of shape or size of an area illuminated by radiation redirected by the surface as a function of change in position between the optical component and the surface; detecting, using a first detector, at least part of the redirected radiation to produce a first detection signal; detecting, using a second detector, at least part of the redirected radiation to produce a second detection signal, wherein the first detector has a first detector radiation receiving element extending in a plane and the second detector has a second detector radiation receiving element extending in substantially the same plane as the first detector radiation receiving element and the first detector radiation receiving element being generally concentric to the second detector radiation receiving element; and deriving a trigger signal as a function of the first and second detection signals.

In an aspect, there is provided a method of manufacturing devices wherein a device pattern is applied to a series of substrates using a lithographic process, the method including inspecting at least a target formed as part of or beside the device pattern on at least one of the substrates using a method as described herein, and controlling the lithographic process for later substrates in accordance with the result of the method.

In an aspect, there is provided a non-transitory computer program product comprising machine-readable instructions for causing a processor to cause performance of a method as described herein.

In an aspect, there is provided a system comprising: an inspection apparatus configured to provide a beam on a measurement target on a substrate and to detect radiation redirected by the target to determine a parameter of a lithographic process; and a non-transitory computer program product as described herein.

In an aspect, there is provided a detection apparatus comprising: a first mask configured to receive at least part of radiation redirected from a surface and passing through an optical component moving relative to the surface, the first mask having an aperture to allow radiation to pass therethrough; a first detector configured to receive redirected radiation passing through the first mask to produce a first detection signal; a second mask configured to receive at least part of the redirected radiation, the second mask having an aperture to allow radiation to pass therethrough, wherein the first mask comprises an aperture located at the intersection of an optical axis of the redirected radiation with the first mask and the second mask comprises an aperture spaced apart from the intersection of the optical axis with the second mask and having an inner periphery further from the optical axis than an outer periphery of the aperture of the first mask; and a second detector configured to receive redirected radiation passing through the second mask to produce a second detection signal.

In an aspect, there is provided a detection apparatus comprising: a first detector configured to detect radiation, the first detector having a first detector radiation receiving element extending in a plane; and a second detector configured to detect radiation, the second detector having a second detector radiation receiving element extending in substantially the same plane as the first detector radiation receiving element and the first detector radiation receiving element being generally concentric to the second detector radiation receiving element.

In an aspect, there is provided a detection apparatus comprising: a mask configured to receive at least part of radiation redirected from a surface and passing through an optical component moving relative to the surface, the mask having an aperture spaced apart from the intersection of an optical axis of the redirected radiation with the mask; a detector configured detect at least part of the redirected radiation after having passed through the aperture of the mask to produce a detection signal; and a control system configured to produce a trigger signal based on which the position of the optical component with respect to the surface is controlled, the trigger signal being a function of a filtered version of the detection signal.

In an aspect, there is provided a detection apparatus comprising: a detector configured detect at least part of radiation redirected from a surface and passing through an optical component moving relative to the surface to produce a detection signal, wherein a shape or size of illuminated area in a pupil, or conjugate thereof, changes as a function of change in position between the optical component and the surface; and a processor system configured to apply a software mask having an aperture spaced apart from the intersection of an optical axis of the redirected radiation with the detector to effectively block processing of radiation received by the detector nearer to the optical axis than the aperture, to produce a trigger signal based on which the position of the optical component with respect to the surface is controlled.

BRIEF DESCRIPTION OF THE DRAWINGS

Embodiments will now be described, by way of example only, with reference to the accompanying drawings in which:

FIG. 4 schematically depicts an example inspection apparatus;

FIG. 5 illustrates the relationship between an illumination spot of an inspection apparatus and a metrology/inspection target;

DETAILED DESCRIPTION

Before describing embodiments in detail, it is instructive to present an example environment in which embodiments may be implemented.

Figure 1:
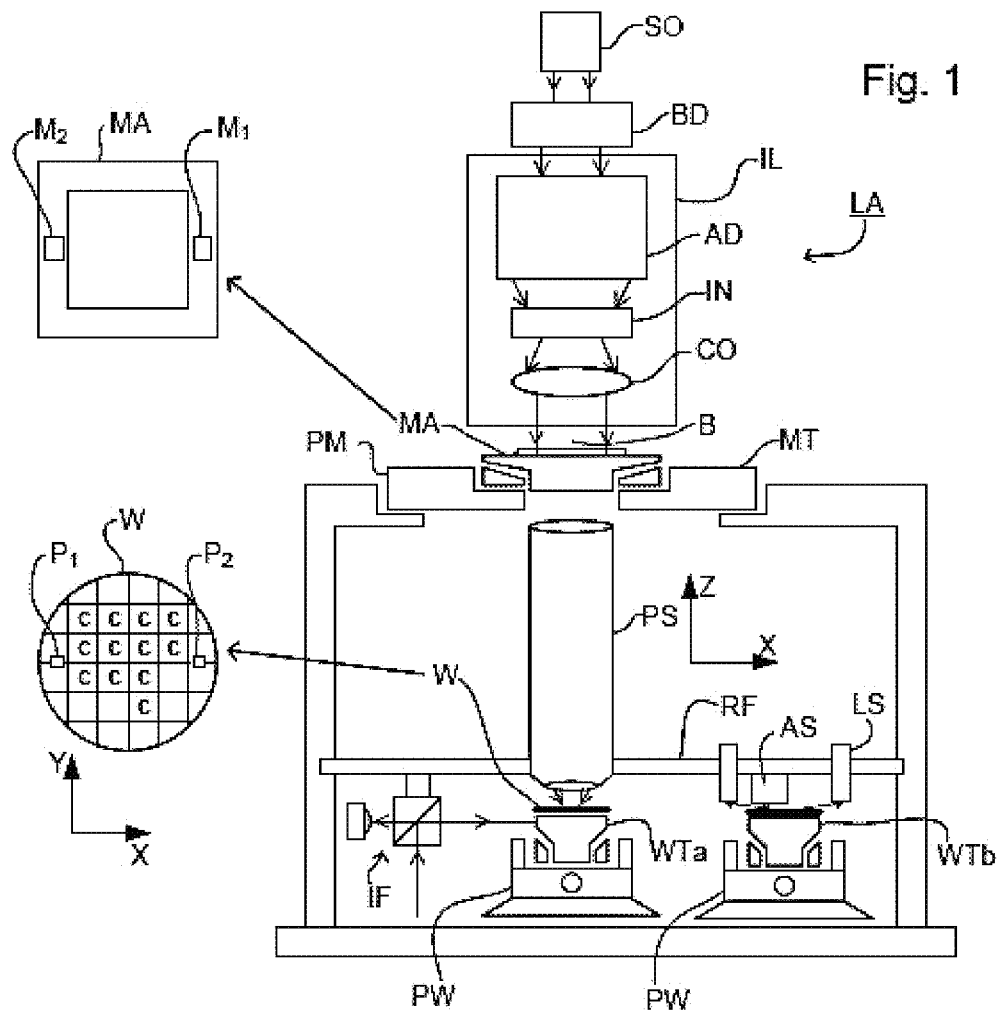
FIG. 1 schematically depicts an embodiment of a lithographic apparatus.

FIG. 1 schematically depicts a lithographic apparatus LA. The apparatus comprises:

an illumination system (illuminator) IL configured to condition a radiation beam B (e.g. UV radiation or DUV radiation).

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W, the projection system supported on a reference frame (RF).

The illumination system may include various types of optical components, such as refractive, reflective, magnetic, electromagnetic, electrostatic or other types of optical components, or any combination thereof, for directing, shaping, or controlling radiation.

The support structure supports the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, deformable mirrors, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more tables (e.g., two or more substrate tables WTa, WTb, two or more patterning device tables, a substrate table WTa and a table WTb below the projection system without a substrate that is dedicated to, for example, facilitating measurement, and/or cleaning, etc.). In such "multiple stage" machines the additional tables may be used in parallel, or preparatory steps may be carried out on one or more tables while one or more other tables are being used for exposure. For example, alignment measurements using an alignment sensor AS and/or level (height, tilt, etc.) measurements using a level sensor LS may be made.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the patterning device and the projection system. Immersion techniques are known in the art for increasing the numerical aperture of projection systems. The term "liquid immersion" as used herein does not mean that a structure, such as a substrate, must be submerged in liquid, but rather only means that liquid is located between the projection system and the substrate during exposure.

Further, the lithographic apparatus may also be of a type wherein at least an optical element is located in close proximity to a portion of the substrate resulting in near-field radiation spanning a gap between the optical element and the substrate. This may be referred to as solid immersion using a solid immersion lens/optical element.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD configured to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PS, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
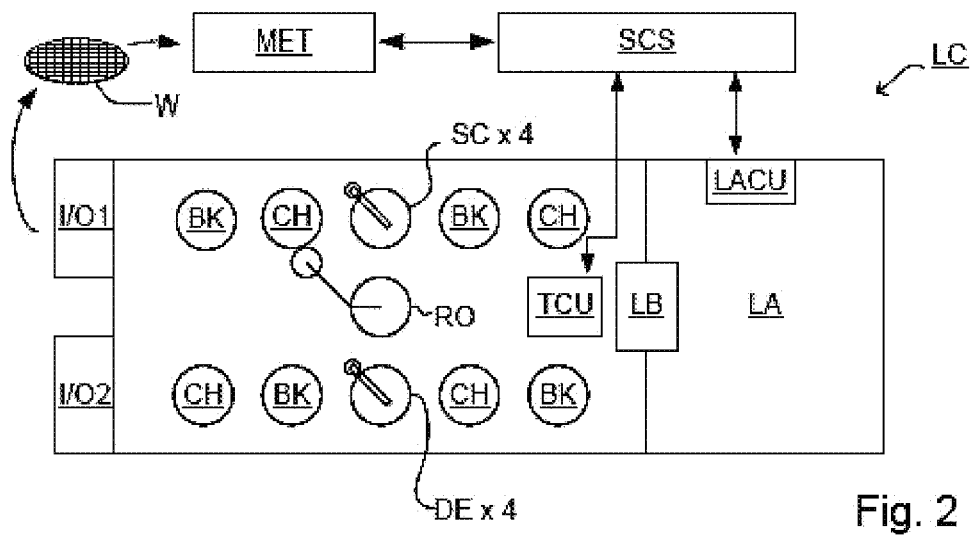
FIG. 2 schematically depicts an embodiment of a lithographic cell or cluster.

As shown in FIG. 2, the lithographic apparatus LA forms part of a lithographic cell LC, also sometimes referred to a lithocell or cluster, which also includes apparatuses to perform pre- and post-exposure processes on a substrate. Conventionally these include one or more spin coaters SC to deposit one or more resist layers, one or more developers DE to develop exposed resist, one or more chill plates CH and/or one or more bake plates BK. A substrate handler, or robot, RO picks up one or more substrates from input/output port I/O1, I/O2, moves them between the different process apparatuses and delivers them to the loading bay LB of the lithographic apparatus. These apparatuses, which are often collectively referred to as the track, are under the control of a track control unit TCU which is itself controlled by the supervisory control system SCS, which also controls the lithographic apparatus via lithography control unit LACU. Thus, the different apparatuses can be operated to maximize throughput and processing efficiency.

In order that a substrate that is exposed by the lithographic apparatus is exposed correctly and consistently, it is desirable to inspect an exposed substrate to measure one or more properties such as overlay error between subsequent layers, line thickness, critical dimension (CD), etc. Accordingly a manufacturing facility in which lithocell LC is located also typically includes a metrology/inspection system MET which receives some or all of the substrates W that have been processed in the lithocell. The metrology/inspection system MET may be part of the lithocell LC, for example it may be part of the lithographic apparatus LA.

Metrology/inspection results may be provided directly or indirectly to the supervisory control system SCS. If an error is detected, an adjustment may be made to exposure of a subsequent substrate (especially if the inspection can be done soon and fast enough that one or more other substrates of the batch are still to be exposed) and/or to subsequent exposure of the exposed substrate. Also, an already exposed substrate may be stripped and reworked to improve yield, or discarded, thereby avoiding performing further processing on a substrate known to be faulty. In a case where only some target portions of a substrate are faulty, further exposures may be performed only on those target portions which are good.

Within a metrology/inspection system MET, an inspection apparatus is used to determine one or more properties of the substrate, and in particular, how one or more properties of different substrates vary or different layers of the same substrate vary from layer to layer. The inspection apparatus may be integrated into the lithographic apparatus LA or the lithocell LC or may be a stand-alone device. To enable rapid measurement, it is desirable that the inspection apparatus measure one or more properties in the exposed resist layer immediately after the exposure. However, the latent image in the resist has a low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of a faulty substrate but may still provide useful information.

Figure 3:
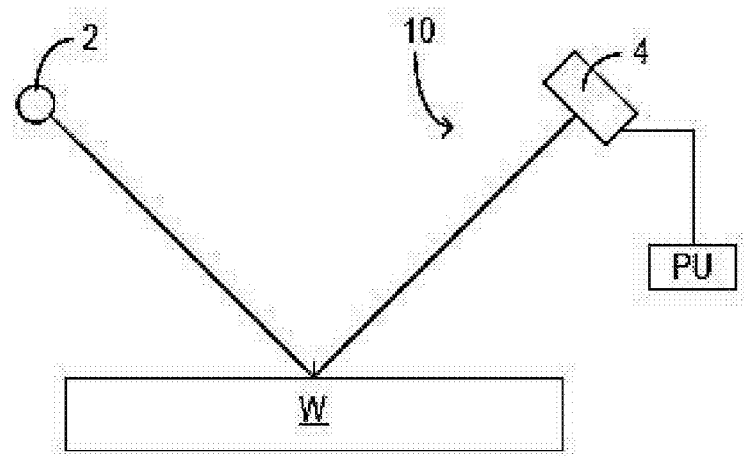
FIG. 3 schematically depicts an example inspection apparatus and metrology technique.
Figure 3:
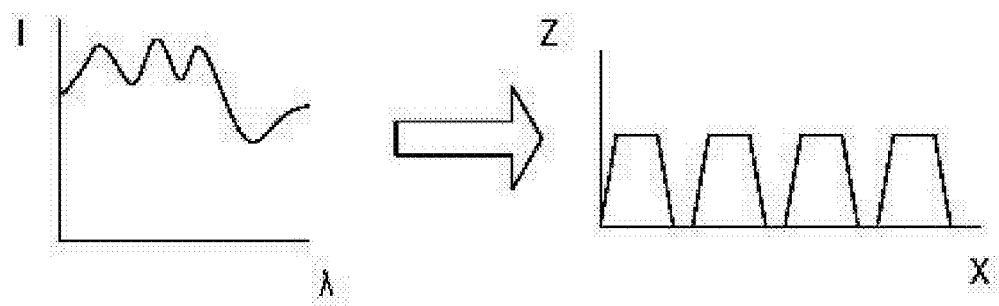

FIG. 3 depicts an example inspection apparatus (e.g., a scatterometer). It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation, as shown, e.g., in the graph in the lower left. From this data, the structure or profile giving rise to the detected spectrum may be reconstructed by processor PU, e.g. by Rigorous Coupled Wave Analysis and non-linear regression or by comparison with a library of simulated spectra as shown at the bottom right of FIG. 3. In general, for the reconstruction the general form of the structure is known and some parameters are assumed from knowledge of the process by which the structure was made, leaving only a few parameters of the structure to be determined from the measured data. Such an inspection apparatus may be configured as a normal-incidence inspection apparatus or an oblique-incidence inspection apparatus.

Another inspection apparatus that may be used is shown in FIG. 4. In this device, the radiation emitted by radiation source 2, which may be coherent or incoherent, is collimated using lens system 12 and transmitted through interference filter 13 and polarizer 17, reflected by partially reflecting surface 16 and is focused into a spot S on substrate W via an objective lens 15, which has a high numerical aperture (NA), desirably at least 0.9 or at least 0.95. A solid immersion inspection apparatus (using near-field radiation between an objective of the apparatus and the target) and/or a liquid immersion inspection apparatus (using a relatively high refractive index fluid such as water) may even have a numerical aperture over 1.

As in the lithographic apparatus LA, one or more substrate tables may be provided to hold the substrate W during measurement operations. The substrate tables may be similar or identical in form to the substrate tables WTa, WTb of FIG. 1. In an example where the inspection apparatus is integrated with the lithographic apparatus, they may even be the same substrate table. Coarse and fine positioners may be provided to a second positioner PW configured to accurately position the substrate in relation to a measurement optical system. Various sensors and actuators are provided for example to acquire the position of a target of interest, and to bring it into position under the objective lens 15. Typically many measurements will be made on targets at different locations across the substrate W. The substrate support can be moved in X and Y directions to acquire different targets, and in the Z direction to obtain a desired location of the target relative to the focus of the optical system. It is convenient to think and describe operations as if the objective lens is being brought to different locations relative to the substrate, when, for example, in practice the optical system may remain substantially stationary (typically in the X and Y directions, but perhaps also in the Z direction) and only the substrate moves. Provided the relative position of the substrate and the optical system is correct, it does not matter in principle which one of those is moving in the real world, or if both are moving, or a combination of a part of the optical system is moving (e.g., in the Z and/or tilt direction) with the remainder of the optical system being stationary and the substrate is moving (e.g., in the X and Y directions, but also optionally in the Z and/or tilt direction).

The radiation redirected by the substrate W then passes through partially reflecting surface 16 into a detector 18 in order to have the spectrum detected. The detector may be located in a back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector may be a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam may be used, for example, to measure the intensity of the incident radiation. To do this, when the radiation beam is incident on the partially reflecting surface 16 part of it is transmitted through the partially reflecting surface 16 as a reference beam towards a reference mirror 14. The reference beam is then projected onto a different part of the same detector 18 or alternatively on to a different detector (not shown).

One or more interference filters 13 are available to select a wavelength of interest in the range of, say, 405-790 nm or even lower, such as 200-300 nm. The interference filter may be tunable rather than comprising a set of different filters. A grating could be used instead of an interference filter. An aperture stop or spatial light modulator (not shown) may be provided in the illumination path to control the range of angle of incidence of radiation on the target.

The detector 18 may measure the intensity of redirected radiation at a single wavelength (or narrow wavelength range), the intensity separately at multiple wavelengths or integrated over a wavelength range. Furthermore, the detector may separately measure the intensity of transverse magnetic- and transverse electric-polarized radiation and/or the phase difference between the transverse magnetic- and transverse electric-polarized radiation.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may be etched into the substrate. The pattern (e.g., of bars, pillars or vias) is sensitive to chromatic aberration in the lithographic projection apparatus, particularly the projection system PS, and illumination symmetry and the presence of such aberration will manifest in a variation in the printed grating. Accordingly, the measured data of the printed grating is used to reconstruct the grating. One or more parameters of the 1-D grating, such as line width and/or shape, or one or more parameters of the 2-D grating, such as pillar or via width or length or shape, may be input to the reconstruction process, performed by processor PU, from knowledge of the printing step and/or other inspection processes.

In addition to measurement of a parameter by reconstruction, angle resolved scatterometry is useful in the measurement of asymmetry of features in product and/or resist patterns. A particular application of asymmetry measurement is for the measurement of overlay, where the target 30 comprises one set of periodic features superimposed on another. The concepts of asymmetry measurement using the instrument of FIG. 3 or FIG. 4 are described, for example, in U.S. patent application publication US2006-066855, which is incorporated herein in its entirety. Simply stated, while the positions of the diffraction orders in the diffraction spectrum of the target are determined only by the periodicity of the target, asymmetry in the diffraction spectrum is indicative of asymmetry in the individual features which make up the target. In the instrument of FIG. 4, where detector 18 may be an image sensor, such asymmetry in the diffraction orders appears directly as asymmetry in the pupil image recorded by detector 18. This asymmetry can be measured by digital image processing in unit PU, and calibrated against known values of overlay.

FIG. 5 illustrates a plan view of a typical target 30, and the extent of illumination spot S in the apparatus of FIG. 4. To obtain a diffraction spectrum that is free of interference from surrounding structures, the target 30, in an embodiment, is a periodic structure (e.g., grating) larger than the width (e.g., diameter) of the illumination spot S. The width of spot S may be over 10 or 20 μm and the target width a and length may be 30 or 40 μm square. The target in other words is 'underfilled' by the illumination, and the diffraction signal is free from interference by product features and the like outside the target itself. The illumination arrangement 2, 12, 13, 17 may be configured to provide illumination of a uniform intensity across a pupil plane of objective 15. Alternatively, by, e.g., including an aperture in the illumination path, illumination may be restricted to on axis or off axis directions.

But, there is demand to reduce the space occupied by metrology targets.

For example, there is a desire to, for example, reduce the width of 'scribe lanes' between target portions C on the substrate, where metrology targets have conventionally been located. Additionally or alternatively, there is a desire, for example, to include metrology targets within the device patterns themselves, to allow more accurate monitoring and correction of variations in parameters such as CD and/or overlay. To this end, alternative methods of diffraction based metrology have been devised more recently. For example, in image-based metrology, two images of the target are made, each using different selected orders of the diffraction spectrum. Comparing the two images, one can obtain asymmetry information. By selecting parts of the images, one can separate the target signal from its surroundings. The targets can be made smaller, and need not be square, so that several can be included within the same illumination spot. Examples of this technique are described in U.S. patent application publications US2011-0027704, US2011-0043791, and US2012-0044470.

In addition to or alternatively to reducing the space occupied by metrology targets, there is demand to improve the nature of the measurements themselves, such as their accuracy. For example, there is a desire to, for example, obtain higher sensitivity of measurement. Additionally or alternatively, there is a desire to, for example, obtain better decoupling between various parameters in the reconstruction described above. For example, it is desired to obtain better values for each of the specific parameters of interest, by reducing or eliminating the effect of measurements associated with one parameter of interest influencing another parameter of interest.

As the demand for size reduction and/or accuracy continues, existing techniques may meet some technical limitations. For example, some methods desire to capture at least the $\pm 1^{st}$ diffraction orders. Taking into account the numerical aperture of the objective 15, this constrains the pitch (L) of a periodic structure of the target. To improve sensitivity and/or to reduce target size, one can consider using shorter wavelengths λ. Further, the target cannot be too small otherwise it will not have enough features to be considered as a periodic structure (e.g., at least 15 lines may be required which taking into account previous constraints may fix the minimum periodic structure size around 5 μm×5 μm). Consequently, overlay, as an example, is measured using periodic structures features (e.g., lines) having dimensions far bigger than those of the product (e.g., device) layout, making overlay measurement less reliable. Ideally the feature line and pitch should have similar dimensions to the product features.

Figure 6:
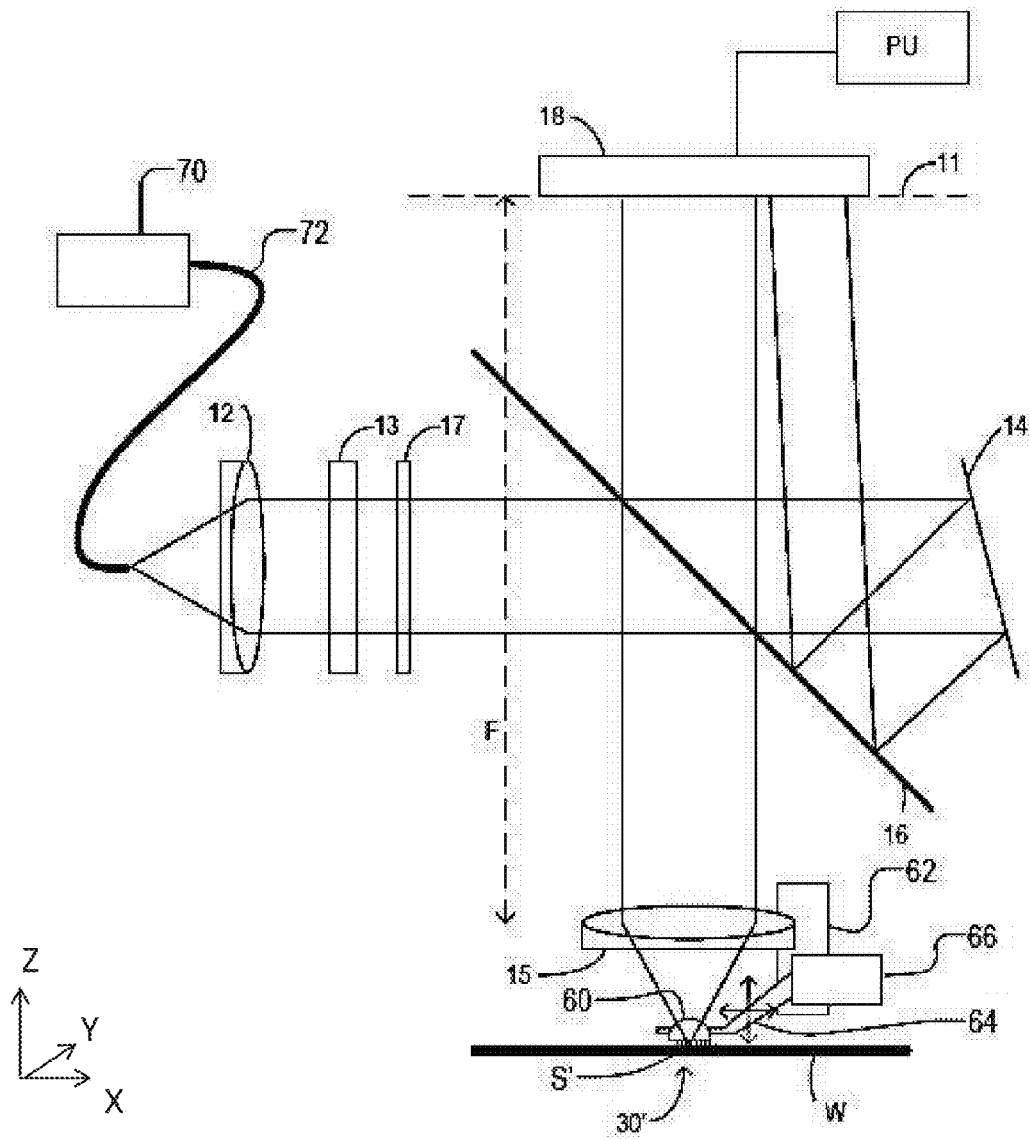
FIG. 6 depicts an example inspection apparatus comprising a solid immersion lens (SIL)

FIG. 6 shows an inspection apparatus in which improvement of the nature of the measurements themselves (e.g., accuracy) and/or reduction of target size may be realized. In FIG. 6, a spot S' (which may be smaller than convention if, for example, a smaller target is desired) can be applied to a target 30' (which may be smaller than convention, e.g., features of smaller pitch, if, for example, a smaller target is desired). Like reference numerals refer to like components throughout the figures.

Comparing the apparatus of FIG. 6 with that of FIG. 4, a first difference is the provision of an additional lens element 60 close to the target 30'. This additional lens is a miniature solid immersion lens (SIL), with a width (e.g., diameter)

only on the order of a millimeter, for example in the range of 1 mm to 5 mm, for example about 2 mm. The SIL comprises, in an example, a hemisphere of material that receives rays of radiation at substantially normal incidence to its surface. In an embodiment, the SIL may be a different shape such as a super-hemisphere. In an embodiment, the SIL is made up of a material of refractive index n, such as glass, fused quartz, a combination of materials, etc. Within the SIL material, the numerical aperture (NA) of the original rays is multiplied by n. The received rays come to focus at about the center of the hemisphere or super-hemisphere and form a spot that is smaller by a factor of n compared to what would have been in the absence of the SIL. For example, a typical glass hemisphere having n=2 will reduce the width of the focused spot by a factor of 2.

Immersion of optical elements in liquid has been used to increase resolution in microscopy and photolithography. The solid immersion lens may achieve similar gains without the inconvenience/problems of liquid immersion. However, to ensure that the smaller spot size does indeed increase the resolution of the system, the bottom of the SIL must either be in contact with the target 30 or positioned extremely closely to it. This restricts its practical applications.

A so-called micro-SIL may also be used. The width (e.g., diameter) of such a SIL is many times smaller, for example about 2 microns in width instead of about 2 millimeters. In an example where SIL 60 in the FIG. 6 apparatus is a micro-SIL, it may have a width (e.g., diameter) less than or equal to 10 μm, potentially less than or equal to 5 μm.

Whether a miniature SIL 60 or a micro-SIL lens is used, it can be attached to a movable support so that controlling the alignment and proximity to the substrate is much simpler than in the case of a lens with bigger width. For example, the SIL 60 in FIG. 6 is mounted to a frame 62. In an embodiment, frame 62 is movable. An actuator may be provided to move frame 62. In an embodiment, the frame 62 supports the objective 15. Accordingly, in an embodiment, the frame 62 may move both the objective 15 and the SIL 60 together. In an embodiment, the actuator for the frame 62 may be configured to move the frame 62 (and the SIL 60) in substantially the Z direction. In an embodiment, the actuator for the frame 62 may be configured to move the frame 62 (and the SIL 60) around the X axis and/or Y axis. In an embodiment, the SIL 60 is in relative fixed position relative to the frame 62. This may be referred to a single stage arrangement, where the objective 15 and SIL 60 are fixed relative to each and are moved by the actuator of frame 62. In such a case, a benefit may be that the SIL can be mechanically positioned in the focus of the objective.

As noted above, the SIL 60 in FIG. 6 is mounted to a frame 62, which in an embodiment supports objective 15. Of course, the SIL 60 may be mounted on a separate frame from that supporting objective 15. In an embodiment, the SIL 60 is connected to a frame (e.g., frame 62) via an arm 64 and actuator 66. Actuator 66 may be, for example, piezoelectric in operation or voice coil actuated. The arrangement where the SIL 60 has an actuator to cause relative movement between a movable objective 15 and the SIL 60 may be referred to as a dual stage arrangement. In a dual stage, certain functionalities may be separated, e.g. separation of motion ranges, vibration suppression capabilities, SIL positioning and focusing with respect to the surface. In an embodiment, the objective stage may move only substantially in the Z-direction (substantially/essentially normal to the surface). In an embodiment, the SIL stage may move in more than 1 degree of freedom, e.g., at least 3 degrees of freedom, e.g., in the Z-direction and around the X-axis and/or the Y-axis, to position the SIL substantially/essentially parallel to the surface. The SIL stage may not have a mechanical range sufficient to cover the desired full travel range. So, the SIL stage can be used to position the SIL at a certain small distance above the surface, while the objective stage can position the objective at focus with respect to the surface, or with respect to the SIL.

Actuator 66 may operate in combination with one or more other actuators positioning the objective as a whole in relation to the target. The servo control loops of these different positioners can be integrated with one another. The components 62, 64 and 66, together with the substrate table and positioners (mentioned above but not shown in FIG. 6), form a support apparatus for positioning the SIL and the target T in close proximity to one another. As noted above, in principle, SIL 60 could be mounted rigidly to the frame 62, and/or may be of larger width. The separate arm and actuator allows easier control of the very small gap, as discussed in more detail below.

Inclusion of the SIL 60 opens the possibility of focusing to a much smaller spot S'. The SIL works by capturing the near-field radiation from the target, and to this end it is positioned substantially closer than one wavelength (λ) of radiation from the target structure, generally closer than a half wavelength, for example around λ/20. The closer the distance, the stronger will be the coupling of near-field signals into the instrument. The gap between the SIL 60 and target 30' may therefore be less than λ/4, for example between λ/40 and λ/8. Because the NA of the inspection apparatus is effectively increased, the pitch of the target periodic structure may be reduced closer to product dimensions.

In examples where a micro-SIL would be used, incoherent radiation of the type conventionally used in, for example, a scatterometer cannot be focused to a micron-sized spot as small as the micro-SIL. Accordingly, in such an embodiment the radiation source 2 may be changed to a coherent source. Therefore a laser source 70 is coupled to illumination optics 12, etc. via an optical fiber 72. The limit on the spot size on the substrate is set by the numerical aperture of the focusing lens system and the laser wavelength. As an additional benefit of using spatially coherent radiation, the instrument with laser radiation source 70 can be used to perform different types of scatterometry or measurement. For example, coherent Fourier scatterometry (CFS) may be used to measure the target.

As highlighted above, a small gap should be maintained between the SIL and the target. As also highlighted above, known techniques for controlling the gap have limitations, particularly when a variety of different target structures and materials are to be inspected.

For example, a significant challenge is to control a relatively small solid immersion lens (SIL) with a gap selected from the range of between λ/40 and λ/4, e.g., 10-100 nm between the SIL and the measured surface with a small (e.g., about 1-10% of the gap size) servo error, subject to possibly much larger vibrations caused by external disturbances, e.g., vibrations of up to 300 nm. This may be achieved with a high-bandwidth control using a signal representative of the gap distance, e.g., a gap error signal (GES).

Figure 7:
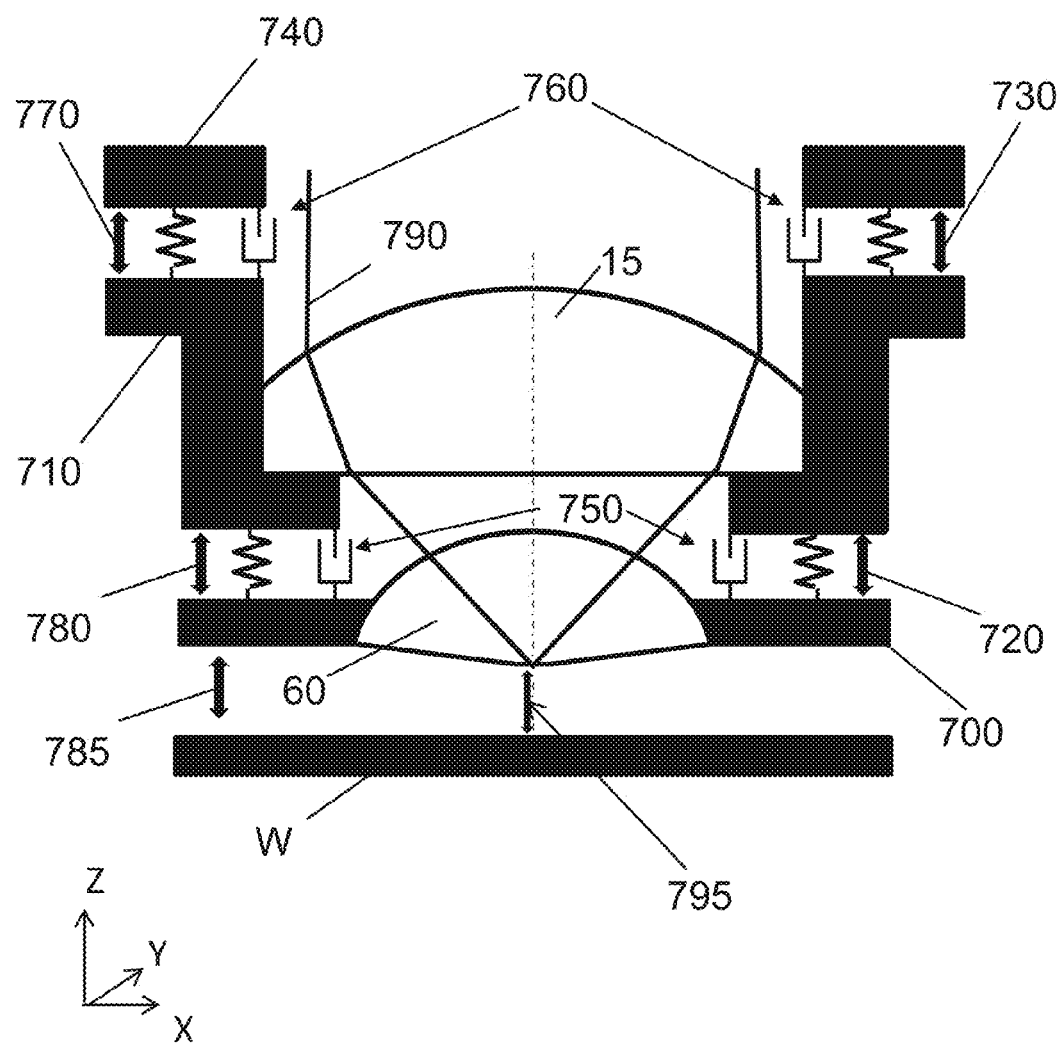
FIG. 7 depicts a schematic diagram of specific components of an inspection apparatus in relation to a target surface.

A "dual stage" concept may be used to facilitate positioning of the SIL and the objective close to the measured surface and allows for certain functionalities to be separated, e.g. separation of motion ranges, vibration suppression capabilities, and/or SIL positioning and focusing with respect to the surface. Referring to FIG. 7, an embodiment of a "dual stage" concept is schematically depicted. A SIL 60 is attached to a movable support 700 to facilitate controlling the alignment and proximity of the SIL 60 to the measured surface, in this case the substrate W. This may be termed the SIL stage. Further, an objective 15 is attached to a movable support 710 to facilitate controlling the alignment and proximity of the SIL 60 and the objective 15 to the measured surface, in this case the substrate W. This may be the objective stage.

An actuator 720 may be provided to move the movable support 700 and the SIL 60 with respect to the movable support 710 and/or objective 15. An actuator 730 may be provided to move the movable support 710 and objective 15 with respect to a support 740. In this embodiment, the movable support 700 is mounted on the movable support 710 and so movement of the movable support 710 may also cause the movable support 700 and/or the SIL 60 to move. Accordingly, in an embodiment, the movable support 710 may move both the objective 15 and the SIL 60 together. Actuator 720 and/or 730 may be, for example, piezoelectric in operation or voice coil actuated.

The SIL stage may be mechanically suspended relative to the objective stage, which is represented by an equivalent spring and/or damping 750. The spring and/or damping 750 may be incorporated in the actuator 720 and/or provided separately by appropriate spring and/or damper structure. Similarly, the objective stage may be mechanically suspended relative to the support 740, which is represented by an equivalent spring and/or damping 760. The spring and/or damping 760 may be incorporated in the actuator 730 and/or provided separately by appropriate spring and/or damper structure.

In an embodiment, the actuator 720 may be configured to move the movable support 700 (and the SIL 60) in substantially the Z direction. In an embodiment, the actuator 720 may be configured to move the movable support 700 (and the SIL 60) around the X axis and/or Y axis. In an embodiment, the actuator 730 may be configured to move the movable support 710 (and the objective 15) in substantially the Z direction. In an embodiment, the actuator 730 may be configured to move the movable support 710 (and the objective 15) around the X axis and/or Y axis. In an embodiment, the objective stage may move only substantially in the Z-direction (substantially normal to the surface). In an embodiment, the SIL stage may move in more than 1 degree of freedom, e.g., at least 3 degrees of freedom, e.g., in the Z-direction and around the X-axis and/or the Y-axis, to position the SIL substantially parallel to the surface. The SIL stage may not have a mechanical range sufficient to cover the desired full travel range. So, the SIL stage can be used to position the SIL at a certain small distance above the surface, while the objective stage can position the objective at focus with respect to the surface, or with respect to the SIL.

Further, in an embodiment, the surface W itself may be moved. For example, a substrate table WT having the surface W may move the surface W relative to the SIL 60 to facilitate establishing an appropriate gap between the SIL 60 and the surface W.

To enable such positioning, one or more signals may be provided. For example, one or more signals 770 may be provided to enable positioning of the objective 15 and/or SIL 60 relative to the support 740 and/or to the surface W. Similarly, one or more signals 780 may be provided to enable positioning of the SIL 60 relative to the objective 15 and/or to the surface W. One or more signals 785 may be provided to enable positioning of the SIL 60 relative to the surface W. As an example, a signal 770 to enable relative positioning between the objective 15 and the support 740 may be provided by an encoder, a gas sensor, or an interferometer. As described in more detail below, a signal 770 to enable relative positioning between the objective 15/SIL 60 and the surface W may be a signal derived from a radiation beam 790 passing through the objective 15, the SIL 60 and onto the surface W. The radiation beam 790 may be a dedicated beam for determining the position or may be the beam used to measure the surface but used for a certain time as a position measuring beam. A signal 780 to enable relative positioning between the objective 15 and the SIL 60 may be a focus error signal (FES). A signal 785 to enable relative positioning between the SIL 60 and the surface W may be a gap error signal (GES) as described herein.

So, the actuators 720 and 730 may operate in combination to position the objective 15 and the SIL 60 in relation to the surface W to establish a desired gap 795. A control system is provided to control positioning of the SIL 60 close to the surface W and to maintain the SIL 60 at or around that position. The control system may receive a setpoint gap value and control one or more actuators (e.g., actuators 720 and/730) to position, in one or more motions, the SIL 60 at or near the setpoint gap value and maintain the SIL 60 at or around that position. There may be significant relative vibrations between the surface W and the SIL 60. So, the SIL 60 may be controlled via a high-bandwidth (e.g., 1-10 kHz) feedback control system. To enable the control by the control system, the gap between the SIL 60 and the surface W may be represented by one or more signals, e.g., a gap error signal (GES). Various techniques for measuring the GES or other position signals are known in the art.

In an embodiment, the actuator 720 may be considered a fine positioner and the actuator 730 may be considered a coarse positioner. In an embodiment for motion in the Z-direction (e.g., vertical motion), a "dual stage" system may enable control of both the (1) focus between the objective 15 and the SIL 60, and (2) the gap 795 between the SIL 60 and the surface W.

Figure 8:
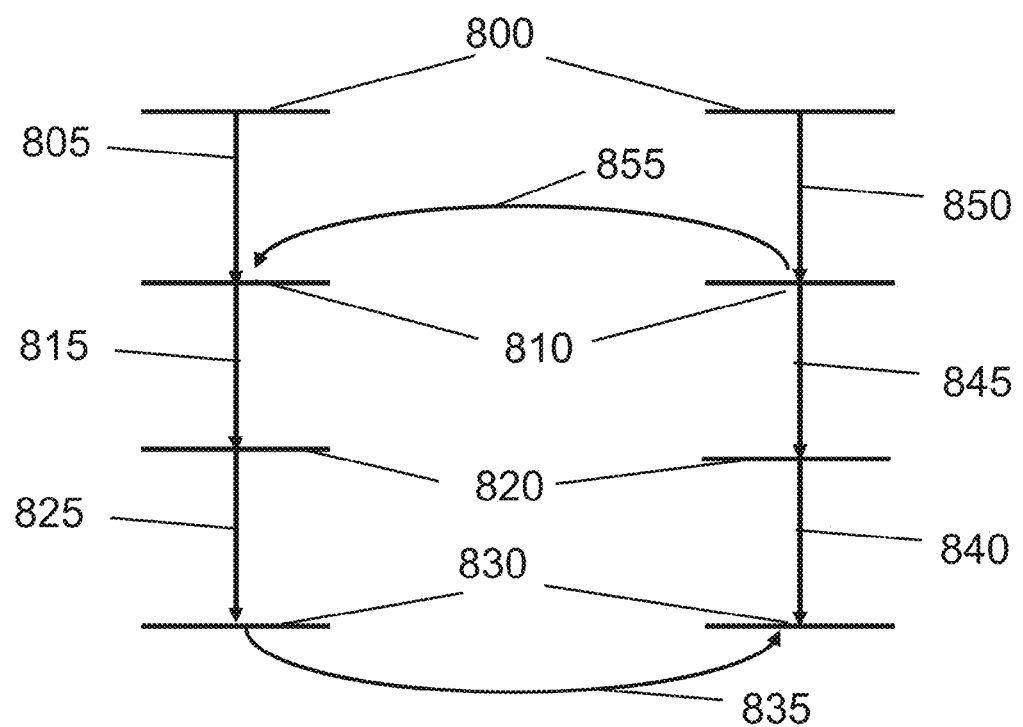
FIG. 8 depicts a schematic representation of various setpoints for relative positioning of various specific components of an inspection apparatus in relation to a target surface.

Further, a "dual stage" system can enable a relatively large dynamic range for the gap 795, e.g., about mm range with sub-10 accuracy. Referring to FIG. 8, an embodiment of Z-direction motion set points is schematically described. A first setpoint distance 800 may be defined for the distance of the SIL 60 from the surface W (i.e., gap 795) to enable exchange of a surface to be measured (e.g., substrate W) with another surface to be measured. In an embodiment, the first setpoint distance 800 may be selected from the range of about several millimeters, e.g., about 1-5 mm, or about 1 mm. Once a surface W to be measured is in place, the SIL 60 may be positioned closer to the surface W in an approach motion 805 to a second setpoint distance 810 of the gap 795. In an embodiment, the second setpoint distance 810 may be selected from the range of about several hundreds of microns, e.g., 400 to 150 microns, e.g., about 250 to 350 microns, e.g., about 300 microns. The second setpoint distance 810 enables relatively safe relative movement between the surface W and the SIL 60, for example, to horizontally position the SIL 60 over a target 30.

From the second setpoint distance 810, the SIL 60 may be positioned closer to the surface W in an approach motion 815 to a third setpoint distance 820 of the gap 795. In an embodiment, the third setpoint distance 820 may be selected from the range of half a wavelength, e.g., about 350 to 125 nanometers, e.g., about 350 to 175 nanometers, e.g., about 300 nanometers. The third setpoint distance 820 may be the maximum gap 795 for which the GES can be used.

From the third setpoint distance 820, the SIL 60 may be positioned closer to the surface W in an approach motion 825 to a fourth setpoint distance 830 of the gap 795. In an embodiment, the fourth setpoint distance 830 may be selected from the range of about 100 to 10 nanometers, e.g., about 50 to 10 nanometers, e.g., about 20-30 nanometers or about 30 nanometers. The fourth setpoint distance 830 may be the gap 795 at which the measurement is taken 835. During the measurement, the gap 795 is substantially maintained at the fourth setpoint distance 830.

Once the measurement is complete, the SIL 60 is positioned further away from the surface W to either enable a further measurement at another location on the surface or exchange of the surface W for another surface W. In an embodiment, the SIL 60 is positioned further away from the surface W in a retraction motion 840 to a third setpoint distance 820, which may have the same value as for the approach motion 825 or may be different therefrom. From the third setpoint distance 820, the SIL 60 is positioned further away from the surface W in a retraction motion 845 to a second setpoint distance 810, which may have the same value as for the approach motion 815 or may be different therefrom.

As noted above, the SIL 60 may be maintained at the second setpoint distance 810 to enable relatively safe relative movement 855 between the surface W and the SIL 60 to, e.g., horizontally position the SIL 60 over a further target 30 by relative movement between the SIL 60 and the target (e.g., moving the surface W horizontally and/or moving the SIL 60 horizontally). So, in an embodiment, for each target at a different location on the surface W, the approach motions 815 and 825 and retraction motions 840 and 845 of the SIL is repeated to help avoid damage of the surface W and the SIL 60 during relative motion between the SIL 60 and the surface W. In an embodiment, the retraction motions 840 and 845 may be combined into a single motion to the second setpoint distance 810, where, for example, the next operation is relative movement 855 between the surface W and the SIL 60 to position the SIL 60 over a further target 30.

If the surface W is being replaced with another surface W or the sensor is being shut down, the SIL 60 is positioned further away from the surface W in a motion 850 to a first setpoint distance 800, which may have the same value as for the start of the motion 805 or may be different therefrom. In an embodiment, the motions 840, 845 and 850 may be combined into a single motion to the first setpoint distance 800, where, for example, the next operation is the surface W being replaced with another surface W or the sensor being shut down.

In an embodiment, the approach motion 805 need not have the same parameters (e.g., acceleration, speed, setpoint, etc.) as the retraction motion 850. Similarly, in an embodiment, the retraction motion 845 need not have the same parameters (e.g., acceleration, speed, setpoint, etc.) as the approach motion 815. Similarly, in an embodiment, the retraction motion 840 need not have the same parameters (e.g., acceleration, speed, setpoint, etc.) as the approach motion 825.

These various motions take time due to, e.g., inertia of moving parts and limitations of the actuator and/or its amplifier. To improve productivity, it is desirable to reduce the time taken within the limits and constraints of the sensor system, the small distances, the control system bandwidth, etc. In particular, "extra" time in the motions 815, 825, 840 and 845 can significantly impact productivity (e.g., number of targets measured per minute).

In an embodiment, the approach velocity in motion 815 may be limiting for the productivity (as well as the approach velocity in motion 805, although the motion 805 occurs less frequently than the approach motion 815). For example, the GES may only be usable to the outer limit of a near-field gap distance (e.g., about 350 to 125 nanometers, e.g., about 300 nm), so the available "braking" distance before the SIL would impact the surface W is relatively short, e.g., a fraction of the about 350 to 125 nanometers, e.g., about 300 nm. So, given that "brake" distance and other conditions of the system, a maximum allowable approach velocity for motions 805 and 815 is determined, e.g., about 100-1000 µm/s, e.g., 250-350 µm/s or about 300 µm/s. So, since the GES may not be usable outside a near-field gap distance, the relative motion between the SIL 60 and surface W would be with that maximum velocity over the full range from the first setpoint distance 800 at the start of each surface W and from the second setpoint distance 810 between targets on a surface W. So, it is desirable to enable a higher velocity at least in motion 815.

Accordingly, in an embodiment, there is provided a multi-step "braking" process. That is, in an embodiment, the relative motion between the SIL 60 and the surface W is "braked" in two or more steps. In a first step, a "far-field braking" is applied using a trigger signal in the range to the second setpoint distance 810 and/or to the third setpoint distance 820. At the third setpoint distance 820, a "near-field braking" is applied by the use of, e.g., the GES signal. With such an approach, the velocity in motion 805 and/or motion 815 can be increased by, e.g., a factor of about 10 times to, e.g., about 1-10 mm/s, e.g., 2.5 to 5 mm/s, e.g., about 3 mm/s. The new maximum allowable velocity may be determined by the brake distance needed due to inertia of the applicable components and by the power electronics (e.g., the brake distance may not exceed the range of the SIL stage). For example, the multi-step brake process may reduce the time for motion 815 by a factor of about 5 times.

In an embodiment, the trigger signal is an optical signal. In an embodiment, radiation 790 that propagates through the objective 15 and the SIL 60, and that is redirected by the surface W and returns through the objective 15 and the SIL 60, is used as the basis for the optical trigger signal. So, with such a signal, the impact on the overall system design is relatively small by using illumination that is already available for, e.g., other control signals, and by using a relatively simple detection method, which has a low impact on the optical path.

Referring to FIG. 9, schematic representations of particular positions of an objective 15 and a SIL 60 in relation to a radiation beam 790 are depicted for determination of a trigger signal. That is, FIGS. 9(A)-(D) show possible ray paths through the objective 15 and the SIL 60. The pupil plane 900 and the focal plane 910 of the objective 15 are depicted as well as the critical angles (CA). In an embodiment, the SIL 60 is hemispherical as shown in FIG. 9. Further, in an embodiment, the SIL 60 has a tip positioned in a central part of the bottom side of the SIL. The tip enables a small gap 795. As discussed further below, the SIL 60 does not need to have a tip as shown. Further, during the relative movement between the SIL 60 and the surface W, the SIL 60 is kept on the focal plane of the objective 15. Also, for ease of depiction, FIG. 9 only illustrates a critical ray at different gaps, in order to illustrate that when the gap reduces, the illuminated radius on the pupil plane increases. Other rays, besides the critical rays depicted, would be provided in a practical implementation of the optical system of FIG. 9.

Figure 9A:
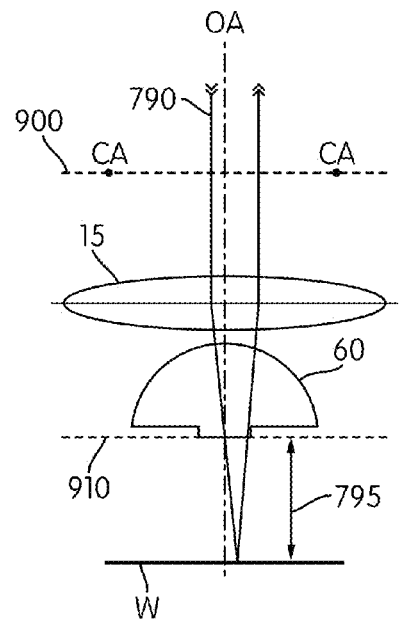
FIGS. 9(A)-9(D) depict schematic representations of particular positions of an objective and a solid immersion lens in relation to a radiation beam.
Figure 9B:
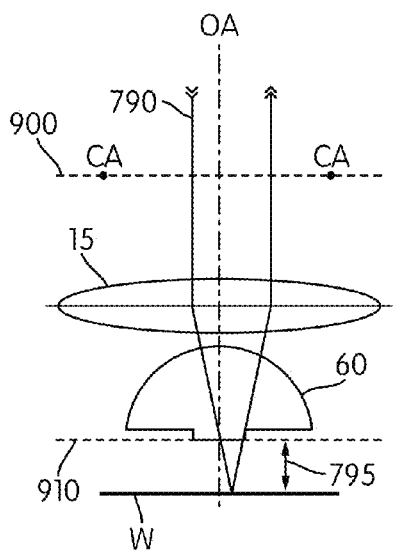

Depending on its position in the pupil plane, a ray of beam 790 can propagate in different ways through the objective 15. Referring to FIG. 9(A), the objective 15 is critically illuminated, and the pupil overfilled. All rays of beam 790 propagate down from the pupil plane 900 towards the SIL 60 and the surface W. If a ray is sufficiently close to the optical axis OA, its redirection from the surface W will be on the tip of the SIL 60, and this ray will propagate back through the objective 15. Referring to FIG. 9(B), showing a gap 795 smaller in distance than in FIG. 9(A), there is a critical position on the pupil plane 900 for which the redirected ray from the surface W illuminates the edge of the tip of the SIL 60 and propagates back through the objective 15.

Figure 9C:
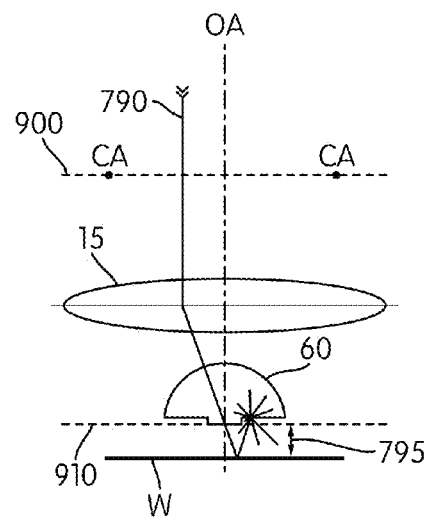
Figure 9D:
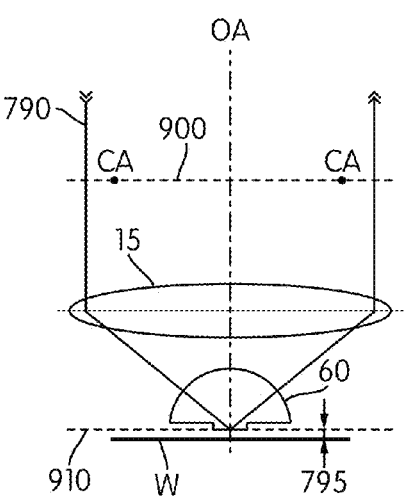

Referring now to FIG. 9(C), showing a size of the gap 795 smaller than in FIG. 9(B), the ray of beam 790 is beyond a critical position, such as the critical position in FIG. 9(B). This ray is vignetted or otherwise completely or partially blocked in the system. This vignetting/blocking can have several causes. An example reason for such vignetting/blocking is due to the beam redirected by the surface W no longer reaching the tip of the SIL 60 as shown in FIG. 9(C). Alternatively or additionally, it could occur further downstream in the optical system. The point is that as long as it is systematic, and does not occur while the surface W is in the focal plane of the objective 15 (i.e., it doesn't occur when the surface W comes into optical contact with the SIL 60, which is in the focal plane), it does not matter what exactly causes the vignetting/blocking. Further, referring to FIG. 9(D), showing a size of the gap 795 smaller than in FIG. 9(C), a ray can be beyond the critical angle CA in the pupil plane 900, and hence, doesn't reach the surface W due to total internal reflection on a surface of the SIL 60.

Because the vignetting/blocking is a property of the optical system, and the optical system is designed and constructed to be stable, the filling of the pupil due to the changing in the size of the gap 795 is highly repeatable, and hence suitable to use for the construction of the trigger signal. So, by reducing the size of the gap 795, the threshold for rays that will propagate back into the SIL 60 will move. So, for example, during the reduction in size of the gap 795, between the optical axis OA and the critical angle CA, the pupil plane will be gradually filled with radiation in a central portion, which radiation is redirected from the surface W.

Figure 10:
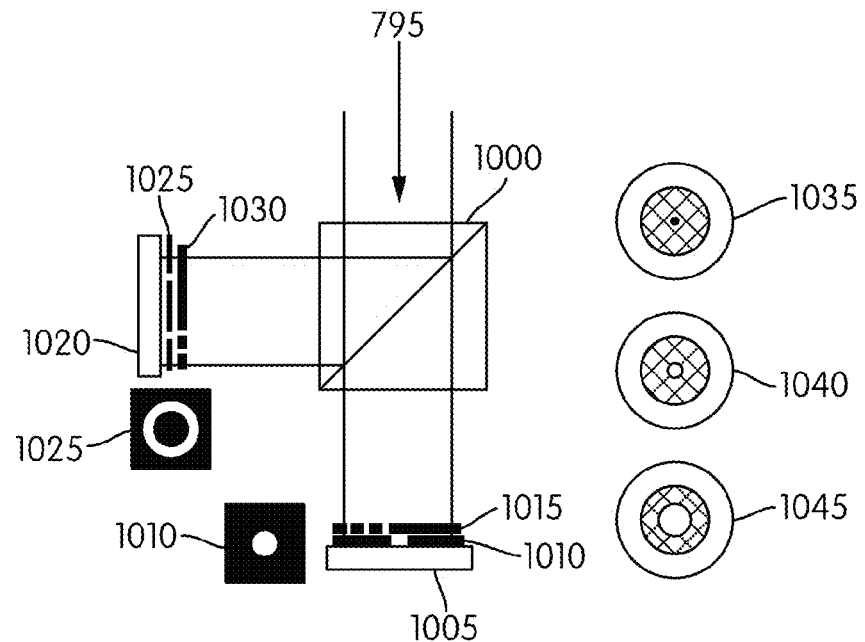
FIG. 10 depicts a schematic representation of a detector system according to an embodiment.

Now, referring to FIG. 10, a schematic representation of a detector system according to an embodiment is depicted that takes advantage of the radiation behaviors in FIG. 9. The detector system comprises a beam splitter 1000 to receive the radiation from the objective 15 (objective 15 and the remainder of the optical system is not shown to enable clearly showing of the components in FIG. 10), whether redirected by surface W, internally reflected, etc. The beam splitter 1000 provides a portion of the radiation towards detector 1005 and a portion of the radiation towards detector 1020. Either or both detector 1005 and detector 1020 may be a photodiode, or a camera sensor. An optical system (not shown) projects the pupil plane 900 of the objective 15 onto a conjugate plane 1015, which is adjacent the detector 1005, and a conjugate plane 1030, which is adjacent the detector 1020.

At or near the conjugate plane 1015, there is provided a mask 1010. Similarly, at or near the conjugate plane 1030, there is provided a mask 1025. In an embodiment, masks 1010 and 1025 are different. Example formats of the mask 1010 and 1025 are shown in the form of their top/bottom views. In an embodiment, the masks 1010, 1025 block all the incident radiation except for radiation that fits within a part left transmissive. In an embodiment, the transmissive parts on mask 1010 and mask 1025 have different radii or widths, with the transmissive part of mask 1010 having a smaller radius or width than the transmissive part of mask 1025. In an embodiment, mask 1010 may comprise a plate with a transmissive opening (e.g., a circular hole such as an open aperture) in a central portion of the plate and mask 1025 may comprise a plate with a transmissive ring opening (e.g., an annulus such as annulus open aperture) around a central portion of the plate.

Referring to the right hand side of FIG. 10, the pupils for three different distances of gap 795 are schematically shown, where the light portions correspond to the radiation reaching the pupil and the dark portions correspond to the empty pupil (i.e., absence of radiation). The pupil 1035 corresponds roughly to the state in FIG. 9(D), where the gap 795 is relatively small. In this pupil 1035, a highly illuminated ring is due to the internal reflection of the SIL 60 beyond the critical angle CA. The pupil 1040 corresponds roughly to a state in FIG. 9(C), where the gap 795 is larger than in FIG. 9(D). So, a significant proportion of the radiation is still at or outside the critical angle CA and so illuminates the ring. Another proportion within the critical angle CA comes within the critical position of the vignetting/blocking described above and thus is redirected through SIL 60 toward the detectors 1005, 1020. This radiation fills in a central portion of the pupil. The pupil 1045 corresponds roughly to another state in FIG. 9(C), where less of the vignetting/blocking occurs and more of the radiation 795 is incident on the surface W and returns back all the way through the optical system to the detectors. The pupil 1045 may be designated as a pupil for a trigger distance, i.e., the point at which a motion may be terminated or begin to be terminated. As the gap 795 is further reduced, more of the central portion of the pupil would become illuminated until there is no effect of the vignetting/blocking (at the transition from, e.g., FIG. 9(C) to FIG. 9(B)) and a solid illumination pupil is formed (corresponding to, e.g., FIG. 9(A)).

So, as the gap 795 is reduced, the pupil plane (angle<critical angle CA) will gradually be filled with radiation, as explained above. Now referring to the masks 1010 and 1025 in FIG. 10, from a certain filling in of a central portion of the pupil onwards, the transmissive part (e.g., hole) on mask 1010 is filled with radiation (and thus detector 1005 is illuminated and emits a signal), but the transmissive part (e.g., the annulus) of mask 1025 is not. Only if and when the gap 795 is closed further, radiation eventually fills the transmissive part (e.g., the annulus) of mask 1025 (and thus detector 1025 is illuminated and emits a signal). A ratio between the signals of detectors 1005 and 1020 may be used to establish a trigger signal (TS) as follows:

$$TS = \frac{V_{PD2}}{V_{PD1} + \varepsilon} \qquad \text{Equation (1)}$$

where $V_{PD2}$ is a signal from detector 1020 (e.g., a voltage signal), $V_{PD1}$ is a signal from detector 1005 (e.g., a voltage signal), and the term E term has a positive value in the order of the noise level of $V_{PD1}$ to avoid a divide-by-zero problem since $V_{PD1} \geq 0$. Other mathematical equations based on $V_{PD1}$ and $V_{PD2}$ could also be suitable as a trigger signal.

Figure 11:
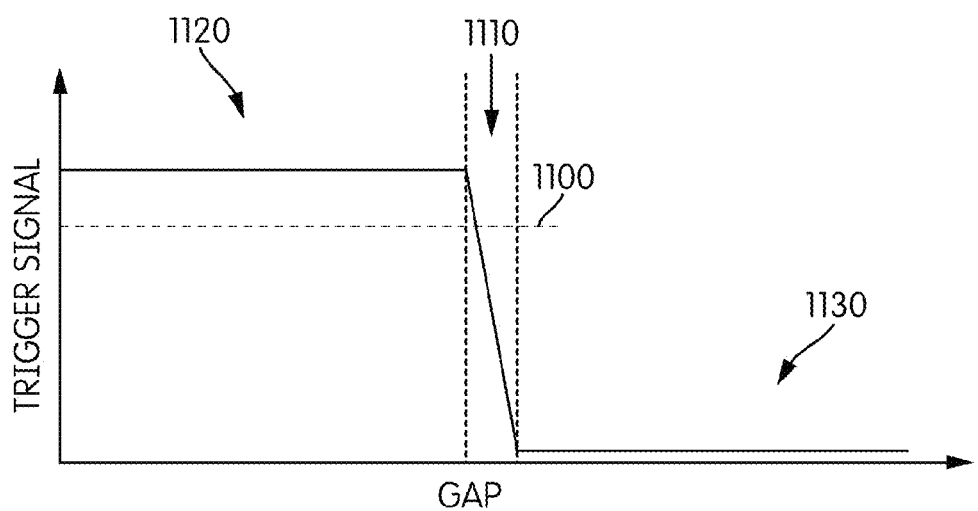
FIG. 11 depicts a simulated schematic graph of a trigger signal versus gap distance according to an embodiment.

The trigger signal can be monitored to determine whether a certain gap distance 795 is obtained. Referring to FIG. 11, a simulated schematic graph of a trigger signal versus gap distance is depicted. In this graph, three general regions can be seen. In a first region, when the distance of the gap 795 begins to be reduced, the distance of the gap 795 is relatively large and only radiation near to the optical axis will be able to propagate back from the surface W to the detectors (e.g., pupil 1035 of FIG. 10). This radiation is weak and only detected by detector 1005 (since mask 1010 has an opening on the optical axis) and so $V_{PD1}$ will have a relatively small value and $V_{PD2}$ will be zero since mask 1025 is substantially opaque on the optical axis. Thus, the trigger signal TS will be in the region marked 1130. The trigger signal TS will be in region 1130 as long as $V_{PD2}$ is zero, irrespective of the value of $V_{PD1}$. Further, the trigger signal TS will be in region 1130 as long as the value of $V_{PD1}$ is relatively larger compared to the value of $V_{PD2}$.

So, if the gap 795 decreases, the value of $V_{PD1}$ will become larger and, due to the small width (e.g., diameter) of the transmissive part of the mask 1010, reach its maximum over a short change in distance of gap 795. But, since $V_{PD1}$ is in the denominator of Equation (1), the trigger signal TS remains 0 as long as $V_{PD2}$ is zero. Once the gap 795 decreases to a size at which radiation also fills the transmissive part of mask 1025, the trigger signal TS will increase in value in transition region 1110. It may reach its maximum quickly in region 1110. Once the maximum values of $V_{PD1}$ and $V_{PD2}$ are reached, i.e., the transmissive parts of masks 1010 and 1025 are fully illuminated with strong radiation, the trigger signal TS will reach its maximum value in region 1120 and remain there for the remainder of the reduction in size of the gap 795. Thus, the region 1130 represents when the distance of the gap 795 is further away from a desired trigger distance of the gap 795 in the transition region 1110, the region 1110 is a small transition range in which the gap size is at, or reaches, the desired trigger distance of gap 795, and the region 1120 represents when the distance of the gap 795 is smaller than the desired trigger distance. So, as shown in FIG. 11, during the reduction in size of the gap 795, the trigger signal TS will show a step-like response making it suitable as a trigger when the trigger signal exceeds, equals or is lower than a certain threshold.

As will be appreciated, a similar graph would be obtained with increase in size of the gap 795 from a small distance of gap 795 to a larger distance. The region 1120 would correspond to the small size of gap 795 and then the signal TS would decrease in transition region 1110 as the size of the gap 795 increases until the signal TS is in region 1130 for a relative larger size of gap 795.

So, as shown in FIG. 11, a threshold 1100 may be defined to have a value in the transition region 1110 and against which the trigger signal TS may be evaluated. For example, for a motion of reducing the size of gap 795, the trigger signal TS may be evaluated as to whether the value is greater than or equal to threshold 1100. When it is greater than or equal to the threshold 1100, an action can be triggered, such as the stop of the relative motion or the beginning of stopping the motion. Similarly, for a motion of increasing the size of gap 795, the trigger signal TS may be evaluated as to whether the value is less than or equal to the threshold 1100. When it is less than or equal to threshold 1100, an action can be triggered, such as the stop of the relative motion, the beginning of stopping the motion, or acceleration of the motion.

To obtain a desired trigger distance of gap 795, the threshold 1100 may be appropriately selected to the desired distance of gap 795 in the transition region 1110 (see FIG. 11). To obtain the actual gap distance that corresponds to the different values of the trigger signal TS, the distance of gap 795 may be separately measured in coordination with determining values of the trigger signal TS (and/or values of $V_{PD1}$ and of $V_{PD2}$) in a calibration step or may be mathematically calculated from first principles or by simulation. Further, to shift the transition region 1110 laterally on the graph of FIG. 11, i.e., to obtain a different range of values of the distance of gap 795 covered by transition region 1110, the design of the transmissive parts of the masks 1010 and 1025 may be altered, e.g., in size and/or shape (also by, for example, a calibration step or by mathematical calculations from first principles or by simulation). In an embodiment, additionally or alternatively, to shift the transition region 1110 laterally on the graph of FIG. 11, i.e., to obtain a different range of values of the distance of gap 795 covered by transition region 1110, the (de)magnification of the conjugated pupil plane may be adjusted (also by, for example, a calibration step or by mathematical calculations from first principles or by simulation).

By using detectors 1005 and 1020, it may avoid directly comparing an amount of reflected radiation to a preset threshold, and with that, may avoid a direct dependence on the reflectivity of the surface W. This reflectivity can vary an order of magnitude, depending on the structures, materials, etc. present on the surface W. So, working with detectors 1005 and 1020, and evaluating their signals with respect to each other, helps make the system more robust against process variations.

In an embodiment, a trigger signal may be generated with one masked detector (e.g., a photodiode) at an image of the pupil of the objective 15. In particular, in an embodiment, a detector with a transmissive ring part in an opaque region is used similar to the detector 1020 and its mask 1025 of FIG. 10. An advantage of this measurement scheme is that the optical path may have only one detector and associated masking. To provide process variation robustness, the single measured signal (e.g., $V_{PD2}$) may be compared with a filtered version of the same signal. In an embodiment, the filtered version may be a low-pass filtered version of the detected signal. If a sudden change in radiation amount at the detector is detected, the detected signal of the detector will change immediately, while a low-pass version of the same signal lags behind. The filtered version of the same signal can be generated electronically or digitally. So, the trigger signal TS may be defined as:

$$TS = \frac{V_{PD}}{V_{filtered} + \varepsilon} \qquad \text{Equation (2)}$$

where $V_{PD}$ is the detected signal of the detector, $V_{filtered}$ is the filtered version of the detected signal, and the term $\varepsilon$ term has a positive value in the order of the noise level of $V_{PD}$ to avoid a divide-by-zero problem since $V_{filtered} \geq 0$. Other mathematical equations based on $V_{PD}$ and $V_{filtered}$ could also be suitable as a trigger signal. For example, further formulations include $$TS = V_{PD} - V_{filtered}, \; TS = \frac{V_{PD}}{V_{lowpass} + \varepsilon}, \text{ or}$$

$$TS = V_{highpass}.$$

Figure 12A:
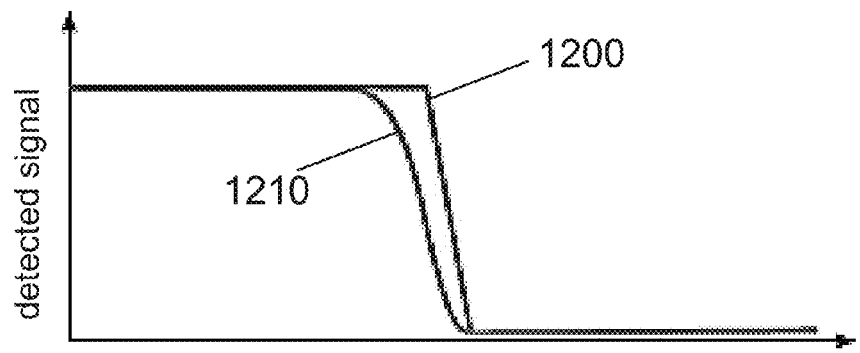
FIG. 12(A) depicts a simulated schematic graph of a detected signal and a filtered version (low-pass in this example) of the detected signal.
Figure 12B:
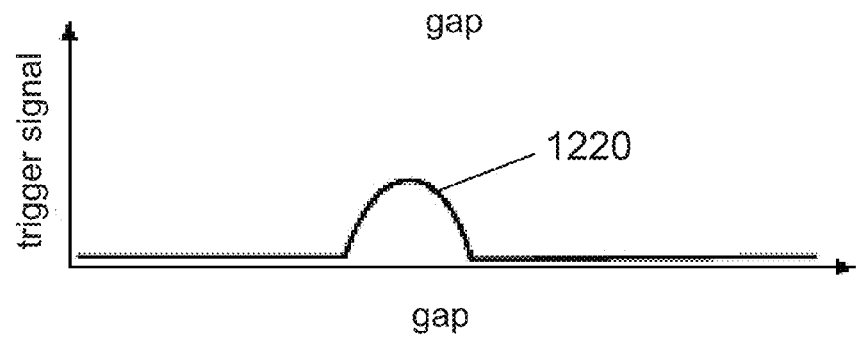
FIG. 12(B) depicts a simulated schematic graph of a trigger signal derived from the detected signal and the filtered version thereof of FIG. 11(A) according to an embodiment.

Referring to FIG. 12, signal 1200 is the detected signal of the detector against the distance of the gap 795. In the example of FIG. 12, signal 1210 is a low-pass version of the detected signal against the distance of the gap 795. As can be seen in the graph, the signal 1210 slightly lags the signal 1200. This lag is taken advantage of in Equation (2) to produce trigger signal 1220. So, the trigger signal 1220 will be zero, unless a sudden change of radiation intensity is detected at the detector. This sudden change can be the trigger to cause an action as described above when the trigger signal equals, exceed or is lower than a certain threshold. The threshold should be carefully selected to be robust against variations in the surface W reflectivity and approach/retract velocity, which determine the trigger signal 1220 peak, and to be robust against measurement noise. The cut-off frequency of the filter should be carefully selected as a function of the approach velocity and the desired width of the TS signal 1220, i.e., the gap range for which TS is larger than zero.

Like in the embodiment of FIGS. 9-11, to obtain a desired trigger distance of gap 795, the threshold for trigger signal 1220 may be appropriately selected to the desired distance of gap 795 in the peak (see FIG. 12). To obtain the actual gap distance that corresponds to the different values of the trigger signal, the distance of gap 795 may be separately measured in coordination with determining values of the trigger signal (and/or values of $V_{PD}$) in a calibration step or may be mathematically calculated from first principles or by simulation. Further, to shift the peak of signal 1220 on the graph of FIG. 12, i.e., to obtain a different range of values of the distance of gap 795 covered by the peak, the design of the transmissive part of the mask may be altered, e.g., in size and/or shape and/or the (de)magnification of the conjugated pupil plane may be adjusted (both or either also by, for example, a calibration step or by mathematical calculations from first principles or by simulation).

In an embodiment, the detectors having differently shaped masks in front of them or the single detector having a mask in front of it may be replaced by a fast detector (e.g., a fast camera) and the "masking" may be performed in software by image processing. Thus, this concept may essentially be the same as the embodiments with one or more detectors having one or more hardware masks, with the one or more masks being implemented in software in combination with a pixelated detector. So, in this embodiment, a fast detector records the same illumination profile that falls on a detector placed at e.g. the position of detector 1020 and/or detector 1005 in FIG. 10. In this embodiment, the mask 1025 and/or 1010 will not be present as physical structures in front of the detector(s), but rather implemented in software with the same shape considerations as the physical masks described above. In an embodiment, the software mask(s) has pixel values of "1" at the transmitting part of a physical hardware mask and has pixel values of "0" at the blocking part of the physical hardware mask. So, in an embodiment, the software mask will then be multiplied with the illumination distribution recorded by the detector pixel by pixel, essentially turning off the pixels corresponding to the blocking part of the applicable mask and keeping on the pixels at the transmitting part of the applicable mask. Thus, the software mask essentially turns the desired pixels off in the recorded detector reading so that the remaining pixels may be used as a detection signal (and processed as described herein).

Figure 13:
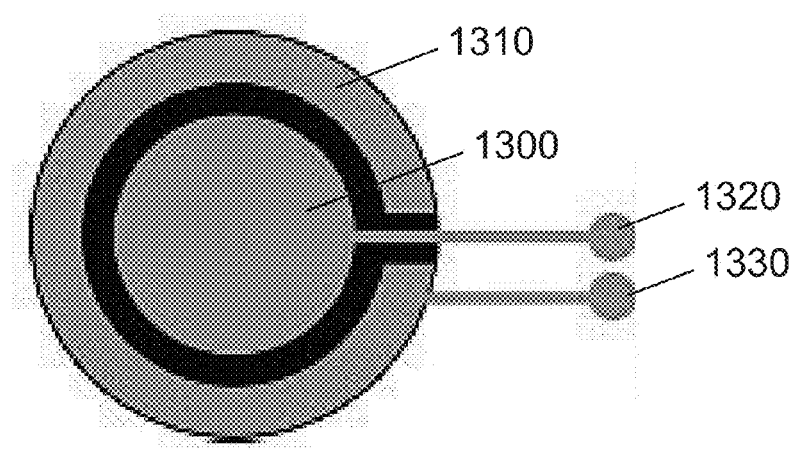
FIG. 13 depicts a schematic representation of a detector system according to an embodiment.

In an embodiment, the trigger signal may be generated using two concentric detectors (e.g., photodiodes) at an image of the pupil of the objective 15. Referring to FIG. 13, there is provided two concentric detectors 1300 and 1310 (e.g., photo diodes). The two detectors 1300, 1310 may be insulated from each other, as shown in FIG. 13. So, if the center is illuminated, the inner detector 1300 will detect the illumination and give an output signal 1320. When the outer detector 1310 is illuminated, it will give a signal 1330. So, the detection of the gradual filling of the pupil, like described in FIG. 9, can be achieved by using the concentric detectors 1300, 1310 instead of a mask. By using a structured detector like this, the radiation path of FIG. 10 can be simplified by eliminating the beam splitter 1000 and the masks 1010 and 1025. The two signals that are generated by this detector arrangement are similar to the signals measured by detectors 1005 and 1020 in the embodiment of FIG. 10, and hence the trigger signal may be derived in a similar fashion as described above and evaluated in a similar manner. Instead of changing the size and/or shape of the masks 1010 and 1025 to change the range of size of the gap 795 measured, the size and/or shape of the detectors 1300 and 1310 may be altered to achieve the same effect. Additionally or alternatively, to change the range of size of the gap 795 measured, the (de)magnification of the conjugated pupil plane may be adjusted. An advantage of the simplified radiation path includes, for example, a more compact design and, because the radiation is not split over multiple arms, the signal detected should be stronger, and therefore, the signal-to-noise ratio should be better.

Figure 14:
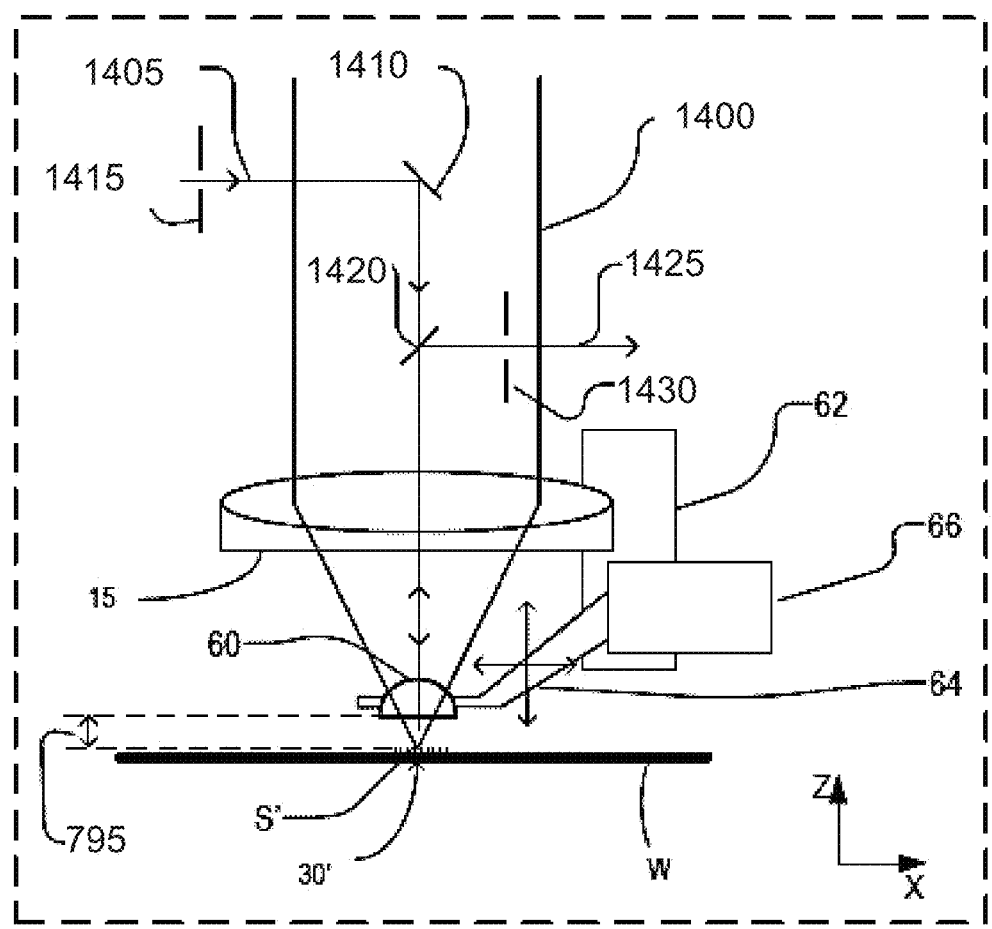
FIG. 14 is an enlarged detail of parts of the apparatus of FIG. 6 showing an embodiment of a gap detection system.
Figure 15:
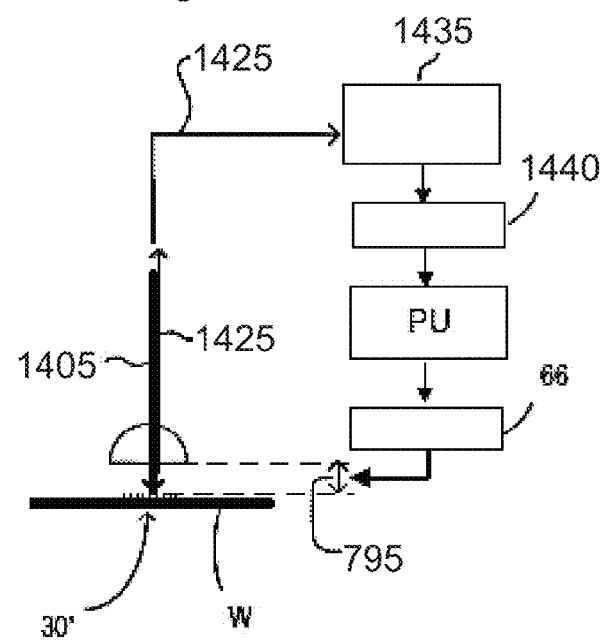
FIG. 15 illustrates schematically a gap detection and control arrangement in the apparatus of FIG. 14.

FIG. 14 shows a schematic partial enlarged view of parts close to the target, in the apparatus of FIG. 6. FIG. 14 in particular provides a schematic view of example optical paths for use in determining and controlling the gap (i.e. the distance of gap 795) in the apparatus of FIG. 6. FIG. 15 shows schematically an embodiment of a gap determining and controlling system. With regard to the function of the apparatus as a metrology or inspection apparatus, a measurement illumination beam 1400 follows an illumination path comprising optical components 12 (not shown in FIG. 14 for convenience), 13 (not shown in FIG. 14 for convenience), 15, 16 (not shown in FIG. 14 for convenience), 17 (not shown in FIG. 14 for convenience), and 60 described above with reference to FIG. 6, and thus will not be discussed here. A collection path comprising optical components 60, 15 to collect radiation redirected by target 30' is also described above with reference to FIG. 6. The radiation collected by optical components of the collection path is directed to a detector 18 (not shown in FIG. 14 for convenience) connected to processor PU (not shown in FIG. 14 for convenience) for target reconstruction or other purposes. As mentioned above, an example application of these parameters may be for determining overlay error. Target 30' may be formed on a substrate W that has been patterned and processed using the lithographic apparatus of FIG. 1 and the cluster of processing tools described above with reference to FIG. 2. The technique disclosed in the present disclosure is not limited to such inspection apparatus. In another application, for example optical recording, illumination paths and collection paths may be similarly arranged.

In an embodiment, to determine and control the gap 795, a radiation beam 1405 (e.g., a broadband radiation beam) follows an optical path that will be referred to as the control path. Beam 1405 may be referred to as a control beam and may be beam 790 described herein, a beam to arrive at the GES, and/or other beam used to determine a distance or position. The control path in this example comprises optical components 1410 and 1420, which may take the form of mirrors or partially-reflective surfaces. Control beam 1405 is directed to SIL 60 by optical component 1410 through optical component 1420. Control beam 1405 may comprise a narrow beam of broadband radiation that passes through SIL 60 to impinge on target 30' at substantially/essentially normal incidence to the substrate surface. The control beam radiation redirected by target 30' is labeled 1425 and is directed by optical component 1420 to a detection arrangement (not shown in FIG. 14 but some examples of which are shown in FIGS. 10 and 13). An aperture 1415 may be placed in the control path to reduce the width of the control beam 1405 so as to increase the coherence length. The width of control beam 1405 may also be varied, for instance, by an optical coating on optical component 1420 so as to select part of the radiation impinging on optical component 1410. An aperture stop 1430 may also be placed in the control path to select a portion of radiation 1425 that is delivered to the detection arrangement.

For convenience of description, the source to generate control beam 1405 is not shown in FIG. 14. A radiation source emitting radiation of one or more wavelengths selected from the ranging of 400 to 900 nm may be used. The source may be, for example, a lamp emitting white light or a so-called white light laser. In other embodiments, the radiation may be polychromatic (comprising many individual wavelengths), rather than having a continuous broad spectrum. The source of the measurement illumination beam 1400 and control beam 1405 may be one and the same. In one such embodiment the laser source 70 of FIG. 6 may be replaced by a broadband light source to supply radiation for both beams 1400 and 1405, when the application does not require the use of a highly coherent light source. Alternatively, different sources may be used to generate beams 1400 and 1405.

FIG. 15 illustrates schematically an arrangement to monitor and control the value of size of gap 795. The arrangement of FIG. 15 includes a detector arrangement 1435 (e.g., such as described above). Radiation 1425 is directed to detector arrangement 1435. The one or more signals produced by detector arrangement 1435 are directed to processor system 1440 which communicates with a processor PU. Processor system 1440 analyzes the one or more signals produced by the detector arrangement to determine, e.g., a distance value of gap 795, a brake, trigger or other signal as described herein and/or one or more setpoints for movement of a component. In an embodiment, such analysis may be performed by processor PU. Processor PU then uses the results of the determination to control the value of gap 795 to a desired set point by activating one or more actuators (e.g., actuator 66). In this way, servo control of the gap 795 is achieved.

Figure 16:
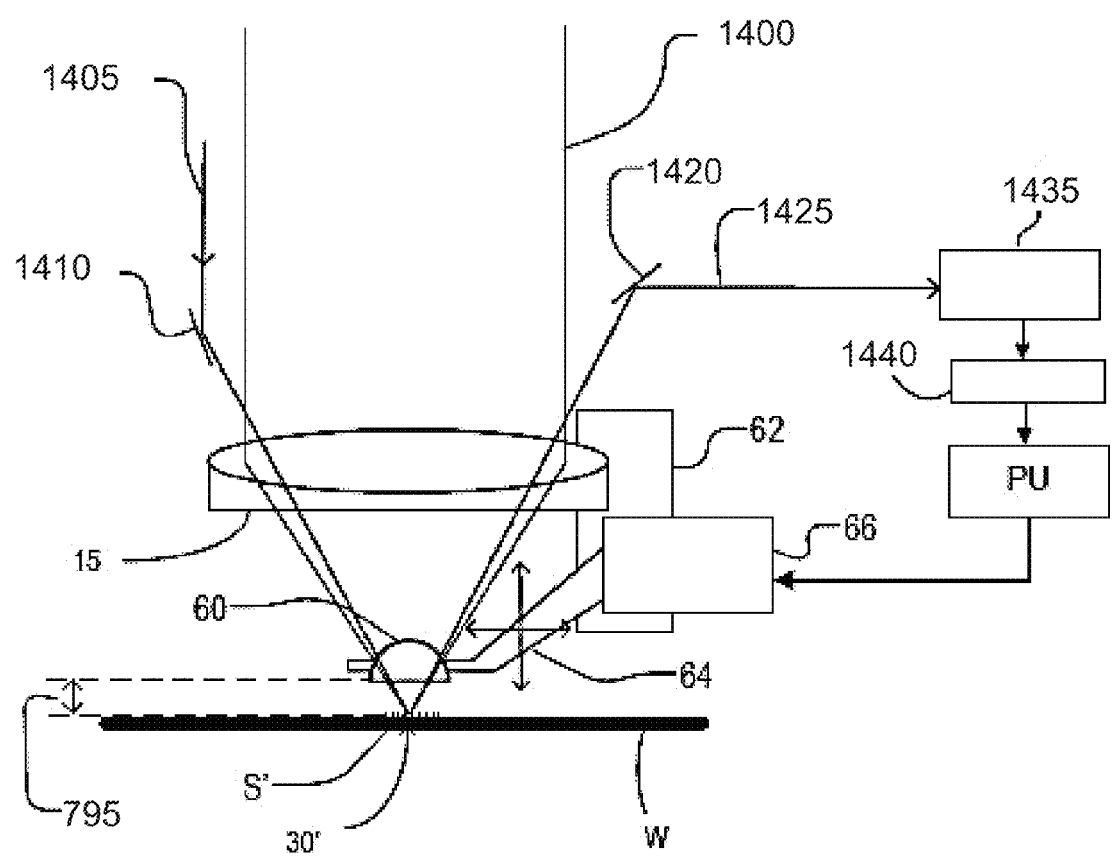
FIG. 16 is an enlarged detail of parts of the apparatus of FIG. 6 showing a further embodiment of a gap detection system.

Further, SIL 60 may be irradiated obliquely by control beam 1405 at an incident angle different from zero. The optical arrangement of FIG. 14 to illuminate the target and collecting the radiation emitted by the target as well as the control path may be adapted accordingly. An example of irradiating SIL 60 and target 30' obliquely by a control beam 1405 is schematically illustrated in FIG. 16. Target 30' is irradiated obliquely to its normal by radiation 1405 via optical component 1410. Radiation 1425 redirected by target 30' is directed to a detection arrangement as described herein.

In an embodiment, a plurality of measurement beams for gap control may be used. For example, there may be a plurality of beams provided, for example, according to the arrangement of FIGS. 14 and 15. There may be a plurality of beams provided, for example, according to the arrangement of FIG. 16. Or, there may be provided a combination of one or more beams provided, for example, according to the arrangement of FIGS. 14 and 15, and one or more beams provided, for example, according to the arrangement of FIG. 16.

Figure 17:
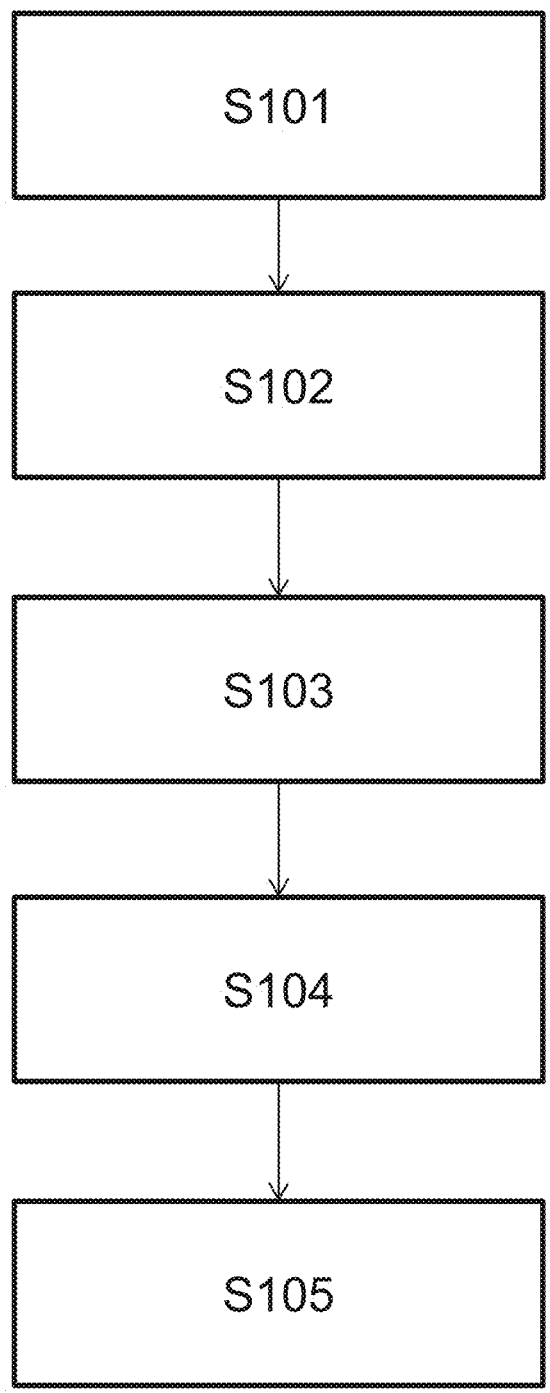
FIG. 17 is a schematic flow chart of an embodiment of a method.

FIG. 17 is a flow chart showing an example method of determining and controlling a gap between components in an optical apparatus. The method in general is implemented by optical and electronic hardware components, in combination with suitable programming instructions provided to a processing system. The gap may be, e.g., a gap between a high numerical aperture optical arrangement and a reflective or diffractive surface, referred to in this example as the target surface. The high numerical aperture optical arrangement may be, for instance, the optical arrangement comprising objective 15 and SIL 60 and the reflective or diffractive surface may be for instance target 30 or 30'. The gap may more generally be between any two components in an optical system.

The method comprises the following steps:

S101: A target structure comprising for example a metrology target on a substrate is positioned, at a predefined position in the X-Y-Z directions, relative to the optical arrangement. A 'coarse' positioning (with an accuracy of the order of mm or microns) of the diffractive surface relative to the high numerical aperture optical arrangement may be performed using other sensors, if necessary to set the gap value for use with, e.g., one or more radiation beams for finer control. Conventional substrate supports and positioning systems can be used for this step. A 'fine' positioning controls the gap by following the steps described, below.

S102: One or more radiation measurement beams are directed through the optical arrangement onto the target surface.

S103: The radiation redirected by the target is collected by the optical arrangement and directed to one or more detector arrangements, such as described above. The detector arrangement(s) produces one or more detection signals based on the radiation received. In an embodiment, there is obtained a first signal by a first position measurement process (e.g., a signal measured as described in the embodiments of FIGS. 9-13) and there is obtained a second signal by a second position measurement process different than the first position measurement process (e.g., a GES signal). In an embodiment, the measurement of S103 may comprise providing radiation through the optical component to reach the surface; blocking at least part of the radiation redirected by the surface to cause a change of shape or size of illuminated area in a pupil, or conjugate thereof, as a function of change in position between the optical component and the surface; and detecting the redirected radiation of the illuminated area.

S104: A processing system analyses the one or more detection signals and determines, e.g., a distance value of gap 795, a brake, trigger or other signal as described herein and/or one or more setpoints for movement of a component. The processing system may further store the analysis output. Steps S102-S104 would be repeated as long as gap control using the measurement beam(s) is needed. For example, in an embodiment, the detected redirected radiation of the illuminated area may be used to produce a trigger signal based on which the position of the optical component with respect to the surface is controlled.

S105: The gap distance 795 is controlled using, or based on, an output of step S104. For example, a distance value of gap 795 may be compared to a set value, and processor PU may then issue commands to cause change in the relative position between one or more parts of the optical arrangement and the target surface. In the example of the inspection apparatus of FIG. 6, the distance of gap 795 may be adjusted using actuator 66. In an embodiment, there is provided control of relative movement between the optical component (e.g., SIL 60) and the surface (e.g., surface W) for a first range of motion (e.g., to setpoint 810 and/or 820) using the first signal described above and there is provided control of relative movement between the optical component and the surface for a second range of motion (e.g., to setpoint 830) using the second signal as described above, the second range of motion being nearer the surface than the first range of motion.

Thus, in an embodiment, there is provided an at least two-step braking system or process for near-field metrology/inspection. There is provided a detection/trigger signal that operates through the objective 15 and SIL 60 (which are already used for metrology/inspection), and that can be obtained by an already available illumination source, and so may minimize the added complexity to the optical system. By operating through the SIL 60, the measurement of the distance between surface W and SIL 60 is performed directly between the SIL 60 and the surface W.

Further, in an embodiment, there is provided a method and system that is robust to process variations (e.g. different reflection coefficients from different surfaces) because, in an embodiment, the signals from at least two detectors are compared with respect to each other, and so no absolute signal may be required. In an embodiment, there is provided a freedom to design the gap distance at which a trigger is caused by, for example, appropriate design of the size and/or shape of the aperture of a mask located in front of a detector of the system and/or appropriate design of the (de)magnification of the conjugated pupil plane.

While embodiments herein have been discussed mostly in relation to approaching surface W (e.g., a surface of target 30/30'), the techniques and apparatus discussed herein may also be used for retraction and/or maintaining the optical component relative to surface W above a certain minimum height.

For example, productivity may be significantly improved by having a retraction distance of gap 795 for movement between targets, e.g., second setpoint distance 810 of the gap 795, be reduced as much as feasible. For example, it may be desirable to reduce the second setpoint distance 810 from the range of about several hundreds of microns to, e.g., in the range of 175-50 microns. The retraction distance of gap 795 is selected to help ensure that the SIL 60 does not hit the surface W during substantially horizontal motion between the surface W and the SIL 60. The retraction distance will depend on numerous variables, such as variation in temperature, variation in substrate table thickness, variation in the substrate thickness and of one or more process layers on the substrate, variation in the positioning of the substrate stage with respect to the SIL 60 in z/Rx/Ry (if a tilted substrate moves, the SIL-substrate distance changes during the motion), and/or dynamic vibrations of the substrate stage and SIL 60.

However, many of these variables may change little during substantially horizontal motion between the surface W and the SIL 60 (or when the SIL 60 and surface W are essentially still with respect to each other). So, where there is little variation, a retraction distance of several hundred microns may be too conservative. But, reducing the retraction distance to in the range of 175-50 microns, e.g., to 50-100 µm or about 70 µm, may bring an unacceptable risk of collision. This risk can be mitigated with an additional "far field gap" sensor.

Thus, in an embodiment, a signal similar to as described above is used (and possibly designed for) the retraction height. So, for example, after an inspection or metrology measurement of the surface W, the size of gap 795 is increased by the relative movement between the SIL 60 and the surface W to the desired retraction height (e.g., 175-50 microns, e.g., to 50-100 µm or about 70 µm) using an encoder, interferometer or other sensor (a sensor with a reference at the sensor stage). Then, during relative horizontal motion between the surface W and the SIL 60, a radiation beam is detected through the optical system as described above for the multiple-step "braking" process and a trigger signal is correspondingly created. So, when the gap reduces in size due to a variation as described above, and reduces to a trigger level e.g., at 50 µm where the retraction height is 70 µm, such that a threshold value is passed for the trigger signal, a trigger can be generated and used to retract, e.g., the SIL 60.

The trigger level should be such that there is sufficient time to respond during relative motion between the surface W and the SIL 60. It should also consider the geometry of the bottom of the SIL 60 and the substrate topology, e.g., the measured distance through the SIL 60 may not be the smallest distance between the SIL 60 and the surface W.

In an embodiment, a multi-step safety mechanism may be provided where 1) at a first trigger level (e.g., 50 µm) the distance of the gap between the surface W and the SIL 60 is increased (e.g., the SIL 60 is retracted), and 2) at a second trigger level (e.g., 30 µm), the relative horizontal motion between the surface W and the SIL 60 is stopped. Thus, the first trigger may allow the relative horizontal motion, whereas the second trigger would effectively be an "emergency" stop (e.g., it may cause a delay in processing).

So, in an embodiment, there may be multiple trigger thresholds associated with different sizes of gap 795. For example, there may be:

1) a "brake" trigger, with its associated size of the gap 795, as described above for an approach toward the surface W, and/or 2) a retraction trigger, with its associated size of the gap 795, to cause relative substantially vertical motion between the SIL 60 and the surface W when the gap 795 is at a height for relative horizontal motion between the SIL 60 and the surface W (e.g., cause an actuator to move SIL 60 away from the surface W), and/or 3) an "emergency" trigger, with its associated size of the gap 795, to cause relative horizontal motion between the surface W and the SIL 60 to be stopped.

In an embodiment, the triggers for 1) and 2), or 1) and 3) may be determined from a same signal. To enable multiple trigger levels (i.e., sizes of gap 795), additional detectors with different mask configurations may be provided. In an embodiment using a detector and a "software" mask, a different software mask may be employed at different points of the relative position between the SIL 60 and the surface W. For example, a first software mask may be used for 1), a second software mask used for 2) and a third software mask used for 3).

In an embodiment, to provide the control described herein, there may be little, or no, impact on mechanical hardware, there may be limited impact on optical hardware, and there may be limited impact on motion control software through extension of a set point generator and applicable signal processing.

As described above, in an embodiment, there were provided various techniques to control the gap by a technique based on one or more specific signals. The techniques have particular applicability in an optical metrology or inspection apparatus such as a scatterometer, an alignment sensor (which determine alignment between alignment mark), an encoder or interferometer (which enable position measurement), and/or a height or level sensor (which enables measuring of the position of a surface), but can be applied in other applications of SILs or in other applications where an object is positioned and/or maintained very close to another object (e.g., in the below 400 nm range). The technique need not be applied exclusively, and could be applied in combination with one or more other techniques, including one or more techniques discussed in the cited documents.

While the various embodiments herein primarily describe position control of a SIL relative to a substrate/target surface, the disclosed methods and apparatus may be used to control the position of any component, such as a microcantilever, relative to any surface.

Reference to the gap is not intended to imply that a medium between SIL 60 and target 30 must be, e.g., air, or even that it must be gaseous. The medium within the gap in any particular implementation may be a vacuum or partial vacuum, any gaseous or liquid medium, whose refractive index meets the requirements of the optical functions of the apparatus.

In an embodiment, there is provided a method of position control of an optical component relative to a surface, the method comprising: obtaining a first signal by a first position measurement process; controlling relative movement between the optical component and the surface for a first range of motion using the first signal; obtaining a second signal by a second position measurement process different than the first position measurement process; and controlling relative movement between the optical component and the surface for a second range of motion using the second signal, the second range of motion being nearer the surface than the first range of motion.

In an embodiment, obtaining the first signal comprises: providing radiation through the optical component to reach the surface; blocking at least part of the radiation redirected by the surface to cause a change of shape or size of illuminated area in a pupil, or conjugate thereof, as a function of change in position between the optical component and the surface; and detecting the redirected radiation of the illuminated area to produce a signal used to derive the first signal. In an embodiment, the detecting comprises: detecting, using a first detector, at least part of the redirected radiation after having passed through an aperture of a first mask to produce a first detection signal; detecting, using a second detector, at least part of the redirected radiation after having passed through an aperture of a second mask to produce a second detection signal; and deriving the first signal as a function of the first and second detection signals. In an embodiment, the first mask comprises an aperture located at the intersection of an optical axis of the redirected radiation with the first mask and the second mask comprise an aperture spaced apart from the intersection of the optical axis with the second mask and having an inner periphery further from the optical axis than an outer periphery of the aperture of the first mask. In an embodiment, the detecting comprises: detecting, using a detector, at least part of the redirected radiation after having passed through an aperture of a mask to produce a detection signal, the aperture spaced apart from the intersection of an optical axis of the redirected radiation with the mask; and deriving the first signal as a function of a filtered version of the detection signal. In an embodiment, the detecting comprises: detecting, using a first detector, at least part of the redirected radiation to produce a first detection signal; detecting, using a second detector, at least part of the redirected radiation to produce a second detection signal, wherein the first detector has a first detector radiation receiving element extending in a plane and the second detector has a second detector radiation receiving element extending in substantially the same plane as the first detector radiation receiving element and the first detector radiation receiving element being generally concentric to the second detector radiation receiving element; and deriving the first signal as a function of the first and second detection signals. In an embodiment, the first signal is a function of the second detection signal divided by the first detection signal. In an embodiment, the method further comprises evaluating the first signal against a threshold and upon the first signal passing the threshold, stopping, or beginning to stop, the relative movement between the optical component and the surface in the first range of motion. In an embodiment, the second signal is a gap error signal (GES). In an embodiment, the method comprises: providing radiation through the optical component to reach the surface; detecting radiation redirected by the surface to produce a signal representative of a size of a gap between the optical component and the surface; and evaluating the signal against a threshold and upon the signal passing the threshold, causing a relative movement between the optical component and the surface to cause in an increase in size of the gap and/or causing a relative horizontal motion between the optical component and the surface to stop.

In an embodiment, there is provided a method of position control of an optical component relative to a surface, the method comprising: providing radiation through the optical component to reach the surface; blocking at least part of the radiation redirected by the surface to cause a change of shape or size of illuminated area in a pupil, or conjugate thereof, as a function of change in position between the optical component and the surface; and detecting the redirected radiation of the illuminated area to produce a trigger signal based on which the position of the optical component with respect to the surface is controlled.

In an embodiment, the detecting comprises: detecting, using a first detector, at least part of the redirected radiation after having passed through an aperture of a first mask to produce a first detection signal; detecting, using a second detector, at least part of the redirected radiation after having passed through an aperture of a second mask to produce a second detection signal; and deriving the trigger signal as a function of the first and second detection signals. In an embodiment, the first mask comprises an aperture located at the intersection of an optical axis of the redirected radiation with the first mask and the second mask comprise an aperture spaced apart from the intersection of the optical axis with the second mask and having an inner periphery further from the optical axis than an outer periphery of the aperture of the first mask. In an embodiment, the detecting comprises: detecting, using a detector, at least part of the redirected radiation after having passed through an aperture of a mask to produce a detection signal, the aperture spaced apart from the intersection of an optical axis of the redirected radiation with the mask; and deriving the trigger signal as a function of a filtered version of the detection signal. In an embodiment, the detecting comprises: detecting, using a first detector, at least part of the redirected radiation to produce a first detection signal; detecting, using a second detector, at least part of the redirected radiation to produce a second detection signal, wherein the first detector has a first detector radiation receiving element extending in a plane and the second detector has a second detector radiation receiving element extending in substantially the same plane as the first detector radiation receiving element and the first detector radiation receiving element being generally concentric to the second detector radiation receiving element; and deriving the trigger signal as a function of the first and second detection signals. In an embodiment, the trigger signal is a function of the second detection signal divided by the first detection signal. In an embodiment, the method further comprises evaluating the trigger signal against a threshold and upon the trigger signal passing the threshold, stopping, or beginning to stop, the movement of the optical component in the first range of motion.

In an embodiment, there is provided a method comprising: providing radiation through an optical component to reach a surface; causing a change of shape or size of an area illuminated by radiation redirected by the surface as a function of change in position between the optical component and the surface; detecting, using a detector, at least part of the redirected radiation after having passed through an aperture of a mask to produce a detection signal, the aperture spaced apart from the intersection of an optical axis of the redirected radiation with the mask; and deriving a trigger signal as a function of a filtered version of the detection signal.

In an embodiment, the trigger signal is a function of the detection signal divided by the filtered version of the detection signal. In an embodiment, the method further comprises evaluating the trigger signal against a threshold and upon the trigger signal passing the threshold, stopping, or beginning to stop, a relative movement between the optical component and the surface. In an embodiment, the filtered version of the detection signal comprises a low-pass version of the detection signal.

In an embodiment, there is provided a method comprising: providing radiation through an optical component to reach a surface; causing a change of shape or size of an area illuminated by radiation redirected by the surface as a function of change in position between the optical component and the surface; detecting, using a first detector, at least part of the redirected radiation to produce a first detection signal; detecting, using a second detector, at least part of the redirected radiation to produce a second detection signal, wherein the first detector has a first detector radiation receiving element extending in a plane and the second detector has a second detector radiation receiving element extending in substantially the same plane as the first detector radiation receiving element and the first detector radiation receiving element being generally concentric to the second detector radiation receiving element; and deriving a trigger signal as a function of the first and second detection signals. In an embodiment, the method further comprises evaluating the trigger signal against a threshold and upon the trigger signal passing the threshold, stopping, or beginning to stop, a relative movement between the optical component and the surface.

In an embodiment, the optical component comprises a solid immersion lens and the surface comprises a measurement target surface. In an embodiment, the method further comprises positioning the optical component within 1 nm to 400 nm of the surface.

In an embodiment, there is provided a method of manufacturing devices wherein a device pattern is applied to a series of substrates using a lithographic process, the method including inspecting at least a target formed as part of or beside the device pattern on at least one of the substrates using a method as described herein, and controlling the lithographic process for later substrates in accordance with the result of the method.

In an embodiment, there is provided a non-transitory computer program product comprising machine-readable instructions for causing a processor to cause performance of a method as described herein.

In an embodiment, there is provided a system comprising: an inspection apparatus configured to provide a beam on a measurement target on a substrate and to detect radiation redirected by the target to determine a parameter of a lithographic process; and a non-transitory computer program product as described herein. In an embodiment, the system further comprises a lithographic apparatus comprising a support structure configured to hold a patterning device to modulate a radiation beam and a projection optical system arranged to project the modulated onto a radiation-sensitive substrate.

In an embodiment, there is provided a detection apparatus comprising: a first mask configured to receive at least part of radiation redirected from a surface and passing through an optical component moving relative to the surface, the first mask having an aperture to allow radiation to pass therethrough; a first detector configured to receive redirected radiation passing through the first mask to produce a first detection signal; a second mask configured to receive at least part of the redirected radiation, the second mask having an aperture to allow radiation to pass therethrough, wherein the first mask comprises an aperture located at the intersection of an optical axis of the redirected radiation with the first mask and the second mask comprises an aperture spaced apart from the intersection of the optical axis with the second mask and having an inner periphery further from the optical axis than an outer periphery of the aperture of the first mask; and a second detector configured to receive redirected radiation passing through the second mask to produce a second detection signal.

In an embodiment, the apparatus further comprises a control system configured to produce a trigger signal based on which the position of the optical component with respect to the surface is controlled, the trigger signal being a function of the first and second detection signals. In an embodiment, the apparatus further comprises a beam splitter configured to receive redirected and to provide at least part of the redirected radiation to the first mask and at least part of the redirected radiation to the second mask. In an embodiment, the optical component comprises a solid immersion lens and the surface comprises a measurement target surface.

In an embodiment, there is provided a detection apparatus comprising: a first detector configured to detect radiation, the first detector having a first detector radiation receiving element extending in a plane; and a second detector configured to detect radiation, the second detector having a second detector radiation receiving element extending in substantially the same plane as the first detector radiation receiving element and the first detector radiation receiving element being generally concentric to the second detector radiation receiving element.

In an embodiment, the first and second radiation receiving elements are insulated from each other. In an embodiment, the second radiation receiving element substantially surrounds the first radiation receiving element.

In an embodiment, there is provided a detection apparatus comprising: a mask configured to receive at least part of radiation redirected from a surface and passing through an optical component moving relative to the surface, the mask having an aperture spaced apart from the intersection of an optical axis of the redirected radiation with the mask; a detector configured detect at least part of the redirected radiation after having passed through the aperture of the mask to produce a detection signal; and a control system configured to produce a trigger signal based on which the position of the optical component with respect to the surface is controlled, the trigger signal being a function of a filtered version of the detection signal.

In an embodiment, the optical component comprises a solid immersion lens and the surface comprises a measurement target surface. In an embodiment, the filtered version of the detection signal comprises a low-pass version of the detection signal.

In an embodiment, there is provided a detection apparatus comprising: a detector configured detect at least part of radiation redirected from a surface and passing through an optical component moving relative to the surface to produce a detection signal, wherein a shape or size of illuminated area in a pupil, or conjugate thereof, changes as a function of change in position between the optical component and the surface; and a processor system configured to apply a software mask having an aperture spaced apart from the intersection of an optical axis of the redirected radiation with the detector to effectively block processing of radiation received by the detector nearer to the optical axis than the aperture, to produce a trigger signal based on which the position of the optical component with respect to the surface is controlled.

The algorithms described in this document may be implemented via coding of a suitable software program to be performed by, e.g., processor PU or its equivalent in the form of a dedicated microprocessor or the like.

Any controllers or control systems described herein may each or in combination be operable when the one or more computer programs are read by one or more computer processors located within at least one component of the lithographic apparatus. The controllers or control systems may each or in combination have any suitable configuration for receiving, processing, and sending signals. One or more processors are configured to communicate with the at least one of the controllers or control systems. For example, each controller or control system may include one or more processors for executing the computer programs that include machine-readable instructions for the methods described above. The controllers or control systems may include a data storage medium for storing such computer programs, and/or hardware to receive such medium. So the controller(s) or control system(s) may operate according the machine readable instructions of one or more computer programs.

Although specific reference may have been made in this text to the use of embodiments of the invention in the context of metrology or inspection apparatus used to inspect or measure items in association with, e.g., optical lithography, it will be appreciated that the methods and apparatus described herein may be used in other applications, for example imprint lithography, the use or manufacture of integrated optical systems, the use or manufacture of guidance and detection patterns for magnetic domain memories, the use or manufacture of flat-panel displays, the use or manufacture of liquid-crystal displays (LCDs), the use or manufacture of thin film magnetic heads, etc. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The terms "radiation" and "beam" used herein encompass all types of electromagnetic radiation, including ultraviolet (UV) radiation (e.g. having a wavelength of less than about 400 nm and greater than about 20 nm, or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, an embodiment of the invention may take the form of a computer program containing one or more sequences of machine-readable instructions describing a method as disclosed herein, or a non-transitory data storage medium (e.g. semiconductor memory, magnetic or optical disk, etc.) or a transitory medium having such a computer program therein. Further, the machine readable instruction may be embodied in two or more computer programs. The two or more computer programs may be stored on one or more different data storage media.

The descriptions above are intended to be illustrative, not limiting. Thus, it will be apparent to one skilled in the art that modifications may be made to the invention as described without departing from the scope of the claims set out below.

What is claimed is:

1. A method of position control of an optical component relative to a surface, the method comprising:
   obtaining a first signal by a first position measurement process, the obtaining the first signal comprising:
   providing radiation through the optical component to reach the surface,
   blocking at least part of the radiation redirected by the surface to cause a change of shape or size of illuminated area in a pupil, or conjugate thereof, as a function of change in position between the optical component and the surface, and
   detecting the redirected radiation of the illuminated area to produce a signal used to derive the first signal;
   controlling relative movement between the optical component and the surface for a first range of motion using the first signal;
   obtaining a second signal by a second position measurement process different than the first position measurement process; and
   controlling relative movement between the optical component and the surface for a second range of motion using the second signal, the second range of motion being nearer the surface than the first range of motion.

2. The method of claim 1, wherein the detecting comprises:
   detecting, using a first detector, at least part of the redirected radiation after having passed through an aperture of a first mask to produce a first detection signal;
   detecting, using a second detector, at least part of the redirected radiation after having passed through an aperture of a second mask to produce a second detection signal; and
   deriving the first signal as a function of the first and second detection signals.

3. The method of claim 2, wherein the first mask comprises an aperture located at the intersection of an optical axis of the redirected radiation with the first mask and the second mask comprise an aperture spaced apart from the intersection of the optical axis with the second mask and having an inner periphery further from the optical axis than an outer periphery of the aperture of the first mask.

4. The method of claim 2, wherein the first signal is a function of the second detection signal divided by the first detection signal.

5. The method of claim 1, wherein the detecting comprises:
   detecting, using a detector, at least part of the redirected radiation after having passed through an aperture of a mask to produce a detection signal, the aperture spaced apart from the intersection of an optical axis of the redirected radiation with the mask; and
   deriving the first signal as a function of a filtered version of the detection signal.

6. The method of claim 1, wherein the detecting comprises:
   detecting, using a first detector, at least part of the redirected radiation to produce a first detection signal;
   detecting, using a second detector, at least part of the redirected radiation to produce a second detection signal, wherein the first detector has a first detector radiation receiving element extending in a plane and the second detector has a second detector radiation receiving element extending in substantially the same plane as the first detector radiation receiving element and the first detector radiation receiving element being generally concentric to the second detector radiation receiving element; and
   deriving the first signal as a function of the first and second detection signals.

7. The method of claim 1, further comprising evaluating the first signal against a threshold and upon the first signal passing the threshold, stopping, or beginning to stop, the relative movement between the optical component and the surface in the first range of motion.

8. The method of claim 1, wherein the second signal is a gap error signal (GES).

9. The method of claim 1, comprising:
   providing radiation through the optical component to reach the surface;
   detecting radiation redirected by the surface to produce a signal representative of a size of a gap between the optical component and the surface; and
   evaluating the signal against a threshold and upon the signal passing the threshold, causing a relative movement between the optical component and the surface to cause in an increase in size of the gap and/or causing a relative horizontal motion between the optical component and the surface to stop.

10. The method of claim 1, wherein the optical component comprises a solid immersion lens and the surface comprises a measurement target surface.

11. The method of claim 1, further comprising positioning the optical component within 1 nm to 400 nm of the surface.

12. A method of manufacturing devices wherein a device pattern is applied to a series of substrates using a lithographic process, the method including inspecting at least a target formed as part of or beside the device pattern on at least one of the substrates using the method of claim 1, and controlling the lithographic process for later substrates in accordance with the result of the method.

13. A non-transitory computer program product comprising machine-readable instructions for causing a processor to cause:
   provision of radiation through an optical component to reach a surface, wherein at least part of the radiation redirected by the surface is blocked to cause a change of shape or size of illuminated area in a pupil, or conjugate thereof, as a function of change in position between the optical component and the surface; and
   detection of the redirected radiation of the illuminated area to produce a trigger signal based on which a position of the optical component with respect to the surface is controlled.

14. A system comprising:
   an inspection apparatus configured to provide a beam on a measurement target on a substrate and to detect radiation redirected by the target to determine a parameter of a lithographic process; and
   the non-transitory computer program product of claim 13.

15. The system of claim 14, further comprising a lithographic apparatus comprising a support structure configured to hold a patterning device to modulate a radiation beam and a projection optical system arranged to project the modulated onto a radiation-sensitive substrate.

16. The computer program product of claim 13, wherein the instructions are further configured to cause:
   control of relative movement between the optical component and the surface for a first range of motion using the trigger signal;
   obtaining of a further signal by a position measurement process different than a position measurement process used to obtain the trigger signal; and
   control of relative movement between the optical component and the surface for a second range of motion using the further signal, the second range of motion being nearer the surface than the first range of motion.

17. A method of position control of an optical component relative to a surface, the method comprising:
   providing radiation through the optical component to reach the surface;
   blocking at least part of the radiation redirected by the surface to cause a change of shape or size of illuminated area in a pupil, or conjugate thereof, as a function of change in position between the optical component and the surface; and
   detecting the redirected radiation of the illuminated area to produce a trigger signal based on which the position of the optical component with respect to the surface is controlled.

18. The method of claim 17, wherein the detecting comprises:
   detecting, using a first detector, at least part of the redirected radiation after having passed through an aperture of a first mask to produce a first detection signal;
   detecting, using a second detector, at least part of the redirected radiation after having passed through an aperture of a second mask to produce a second detection signal; and
   deriving the trigger signal as a function of the first and second detection signals.

19. A method comprising:
   providing radiation through an optical component to reach a surface;
   causing a change of shape or size of an area illuminated by radiation redirected by the surface as a function of change in position between the optical component and the surface;
   detecting, using a detector, at least part of the redirected radiation after having passed through an aperture of a mask to produce a detection signal, the aperture spaced apart from the intersection of an optical axis of the redirected radiation with the mask; and deriving a trigger signal as a function of a filtered version of the detection signal.

20. The method of claim 19, wherein the trigger signal is a function of the detection signal divided by the filtered version of the detection signal.

* * * * *